United States Patent
Stevenson

(10) Patent No.: US 6,424,234 B1
(45) Date of Patent: Jul. 23, 2002

(54) ELECTROMAGNETIC INTERFERENCE (EMI) FILTER AND PROCESS FOR PROVIDING ELECTROMAGNETIC COMPATIBILITY OF AN ELECTRONIC DEVICE WHILE IN THE PRESENCE OF AN ELECTROMAGNETIC EMITTER OPERATING AT THE SAME FREQUENCY

(75) Inventor: Robert A. Stevenson, Canyon Country, CA (US)

(73) Assignee: Greatbatch-Sierra, Inc., Clarence, NY (US)

( * ) Notice: Subject to any disclaimer, the term of this patent is extended or adjusted under 35 U.S.C. 154(b) by 0 days.

(21) Appl. No.: 09/396,021

(22) Filed: Sep. 15, 1999

Related U.S. Application Data

(60) Provisional application No. 60/100,988, filed on Sep. 18, 1998.

(51) Int. Cl.$^7$ ................................................. H01G 4/35
(52) U.S. Cl. ........................ 333/182; 333/185; 361/302
(58) Field of Search ................................. 361/302, 303, 361/309; 333/183, 184, 185, 167, 182, 132, 181; 174/52.2

(56) References Cited

U.S. PATENT DOCUMENTS 2,756,375 A    7/1956  Peck (List continued on next page.)

FOREIGN PATENT DOCUMENTS

WO    WO 97/12645    * 4/1997 .......... A61N/1/375

Primary Examiner—Robert Pascal
Assistant Examiner—Dean Takaoka
(74) Attorney, Agent, or Firm—Kelly Bauersfeld Lowry & Kelley, LLP

(57) ABSTRACT

A novel electromagnetic interference (EMI) filter is designed to attenuate one or more specific frequencies in order to provide electromagnetic compatibility of an electronic device while in the presence of an electromagnetic emitter operating at the same or similar frequencies. The EMI filter of the present invention combines an EMI low pass filter with one or more "notch" EMI filters tuned to the specific frequencies of interest. When combined in this fashion, the notch EMI filter can effectively attenuate the electromagnetic field of a powerful low frequency emitter which is outside the effective attenuation frequency range of the low pass filter, which is itself effective at filtering a broad range of higher frequencies. In a preferred embodiment, the notch EMI filter capacitive element is integrated in a co-planar relationship with a ceramic feedthrough filter capacitor assembly. This combined notch and low pass filter arrangement is particularly effective in an implantable medical device such as a cardiac pacemaker or implantable cardioverter defibrillator (ICD) against passage of external interference signals, such as those caused by both digital cellular phones and electronic article surveillance systems operating at low frequencies.

46 Claims, 17 Drawing Sheets

U.S. PATENT DOCUMENTS

| | | |
|---|---|---|
| 3,235,939 A | 2/1966 | Rodriguez et al. |
| 3,680,011 A * | 7/1972 | Adams et al. ............... 333/167 |
| 3,781,718 A * | 12/1973 | Gittinger .................... 333/118 |
| 3,920,888 A | 11/1975 | Barr |
| 4,021,760 A * | 5/1977 | Campi ........................ 333/167 |
| 4,083,022 A | 4/1978 | Nijman |
| 4,148,003 A | 4/1979 | Colburn et al. |
| 4,152,540 A | 5/1979 | Duncan et al. |
| 4,220,813 A | 9/1980 | Kyle |
| 4,247,881 A | 1/1981 | Coleman |
| 4,314,213 A | 2/1982 | Wakino |
| 4,352,951 A | 10/1982 | Kyle |
| 4,362,792 A | 12/1982 | Bowsky et al. |
| 4,421,947 A | 12/1983 | Kyle |
| 4,424,551 A | 1/1984 | Stevenson |
| 4,456,786 A | 6/1984 | Kyle |
| 4,737,601 A | 4/1988 | Gartzke |
| 4,741,710 A | 5/1988 | Hogan et al. |
| 5,032,692 A | 7/1991 | DeVolder |
| 5,070,605 A | 12/1991 | Daglow et al. |
| 5,333,095 A | 7/1994 | Stevenson et al. |
| 5,751,539 A | 5/1998 | Stevenson et al. |
| 5,838,216 A * | 11/1998 | White et al. ................. 333/182 |
| 5,896,267 A * | 4/1999 | Hittman et al. ............. 361/302 |
| 5,905,627 A | 5/1999 | Brendel et al. |
| 5,999,398 A * | 12/1999 | Makl et al. ................. 361/302 |

* cited by examiner

PRIOR ART EMI FILTER

PRIOR ART EMI FILTER

WHERE  C = CAPACITY IN FARADS
L = INDUCTANCE IN HENRYS
R = RESISTANCE (INCLUDES RESISTANCE OF INDUCTOR, HOOK-UP WIRE & CAPACITOR EQUIVALENT SERIES RESISTANCE (ESR))

RESONANT FREQUENCY = $F_r$

WHERE $F_R = \dfrac{1}{2\pi\sqrt{LC}}$

WHERE $F_R$ IS IN HERTZ

NUMERICALLY  $L_1$ (IN HENRIES) = $C_2$ (IN FARADS)

$C_1$ (IN FARADS) = $L_2$ (IN HENRIES)

LINE TO LINE $$L_{TOTAL} = L_T = L_1 + L_2 = x + y \text{ HENRIES}$$

$$C_{TOTAL} = C_T = \cfrac{1}{\cfrac{1}{C_1} \cfrac{1}{C_2}} = \cfrac{1}{\cfrac{1}{x} \cfrac{1}{y}} = \cfrac{1}{\cfrac{y+x}{xy}} = \cfrac{xy}{x+y}$$

$$f_r = \frac{1}{2\Pi\sqrt{L_T C_T}} = \frac{1}{2\Pi\sqrt{(x+y)\left[\frac{xy}{(x+y)}\right]}} = \frac{1}{2\Pi\sqrt{xy}}$$

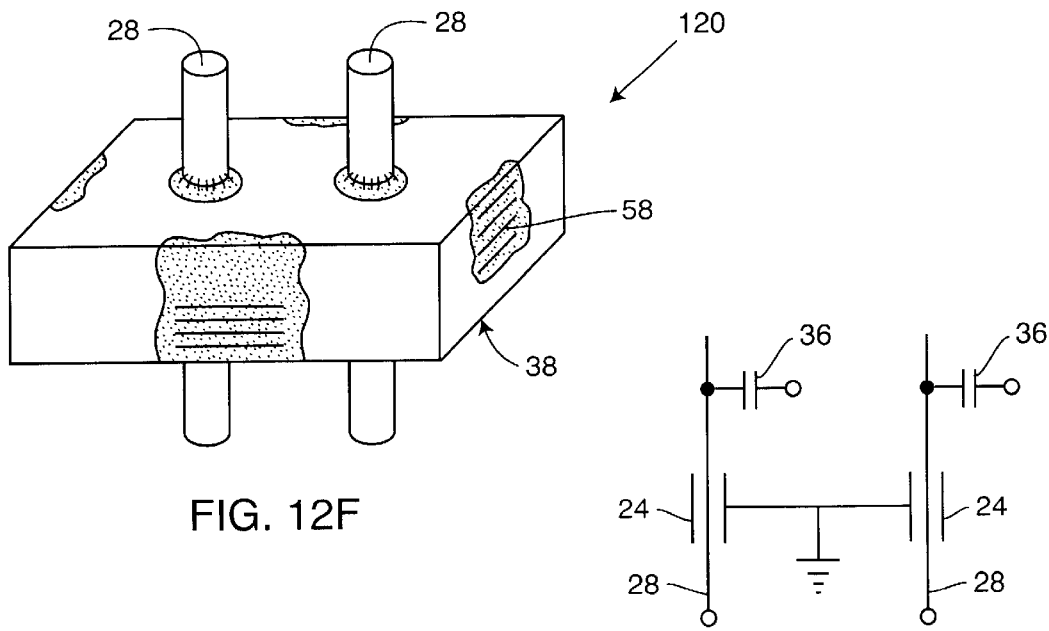
FIG. 12F
FIG. 12G
FIG. 13B
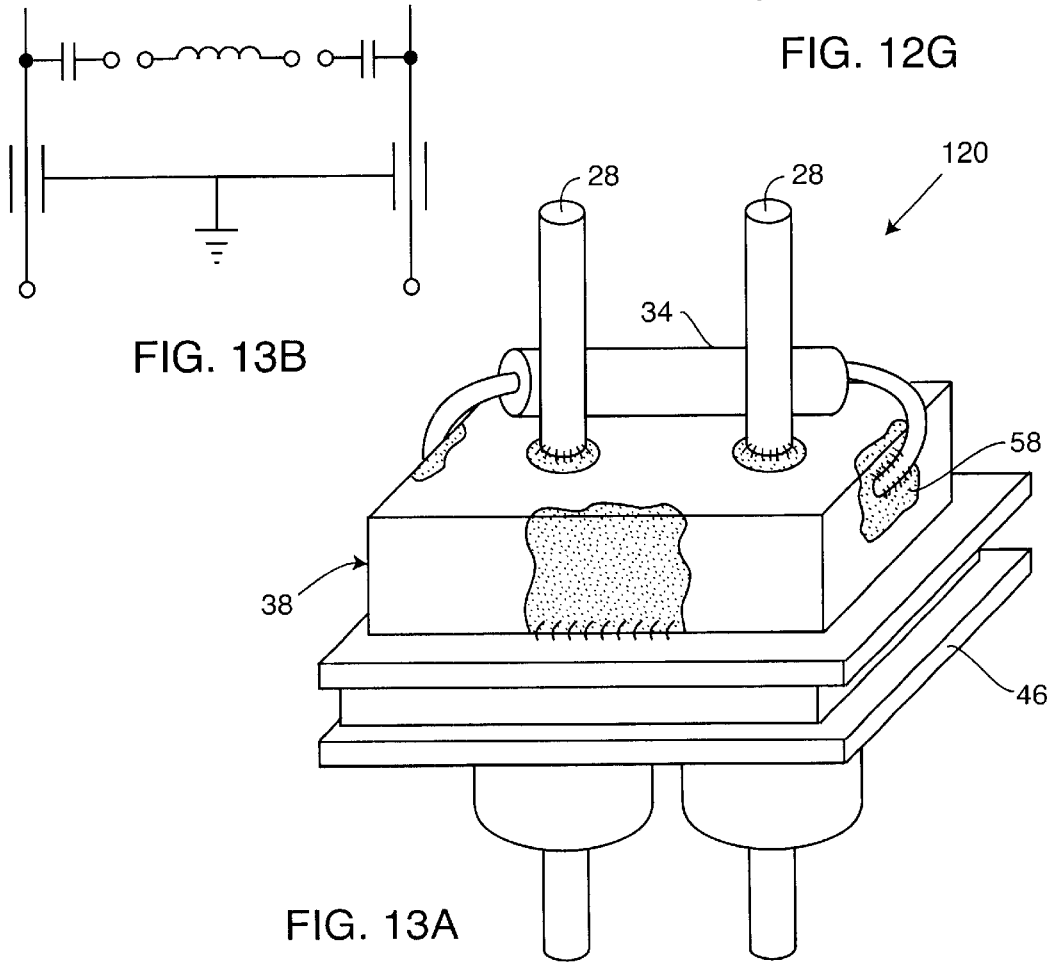
FIG. 13A

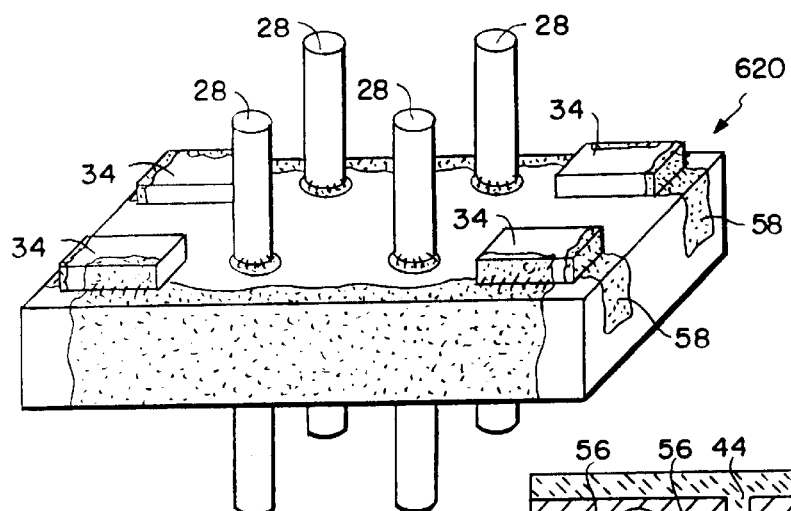
FIG.18A
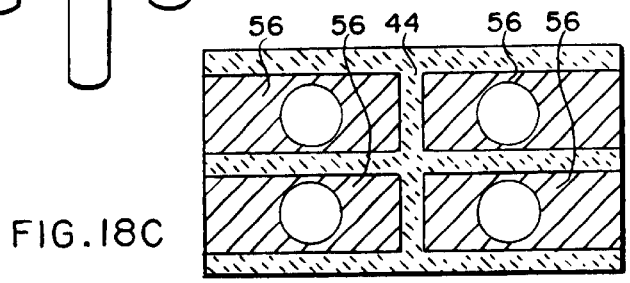
FIG.18C
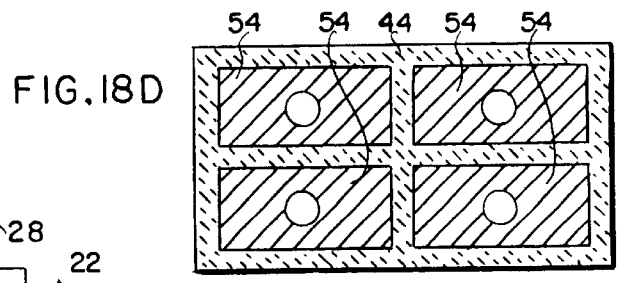
FIG.18D
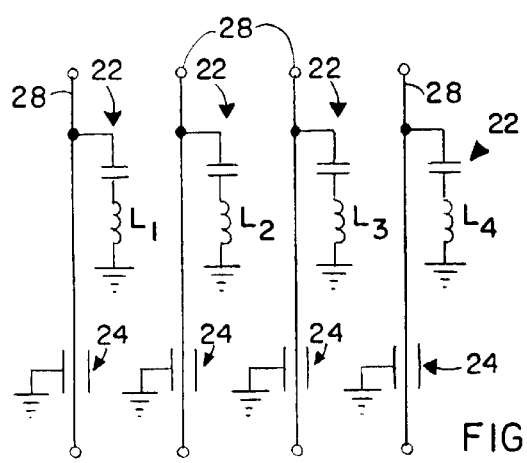
FIG.18B
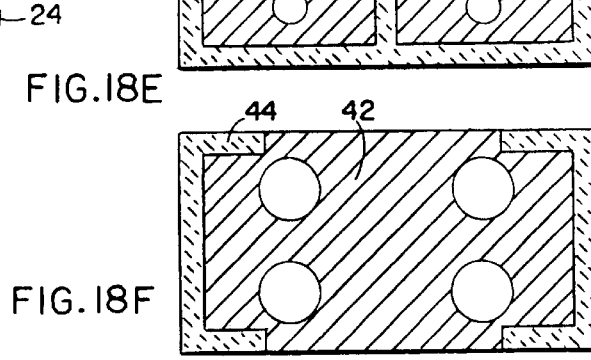
FIG.18E
FIG.18F

ELECTROMAGNETIC INTERFERENCE (EMI) FILTER AND PROCESS FOR PROVIDING ELECTROMAGNETIC COMPATIBILITY OF AN ELECTRONIC DEVICE WHILE IN THE PRESENCE OF AN ELECTROMAGNETIC EMITTER OPERATING AT THE SAME FREQUENCY

RELATED APPLICATION

This application claims priority from provisional application No. 60/100,988, filed Sep. 18, 1998.

BACKGROUND OF THE INVENTION

This invention relates generally to capacitive electromagnetic interference (EMI) filters. More particularly, the present invention relates to a novel electromagnetic interference (EMI) filter which is designed to attenuate one or more specific frequencies in order to provide electromagnetic compatibility of an electronic device (such as a cardiac pacemaker) while in the presence of an electromagnetic (EM) emitter operating at the same or similar frequencies (such as an electronic article surveillance (EAS) system).

Capacitive EMI low pass filters are well know in the art as described in the U.S. patents to Stevenson U.S. Pat. No. 4,424,551, Stevenson U.S. Pat. No. 5,333,095, Rodriguez U.S. Pat. No. 3,235,939, Coleman U.S. Pat. No. 4,247,881, and Duncan U.S. Pat. No. 4,152,540. Low pass filters may be single (single capacitive element) or multi-element (combination of capacitors with inductors or resistors), and are designed to allow low frequency signals to pass with little to no attenuation while at the same time providing a high degree of attenuation at higher frequencies.

An example of an effective low pass filter would be one operating on the 400 Hz power line of an aircraft. The filter would allow the 400 Hz power line frequency to pass through unimpeded while providing over 80 dB of attenuation to undesirable EM signals in the frequency range from 10 KHz to 10 GHz. Unfortunately, such a filter is physically quite large as it requires a number of inductive (L) and capacitive (C) elements. This is simply not practical for many electronic devices such as cardiac pacemakers, where space and weight are at a premium. Even if such a large filter could be fitted inside a cardiac pacemaker, the frequency range below 10 KHz is unprotected and is thereby potentially susceptible to EMI. Another key design constraint for implantable medical devices, which derive their energy needs from batteries, is energy conservation. Because of this, filter designs that employ resistors or low frequency dissipative elements are undesirable.

Broadband low pass EMI filters that are widely used in cardiac pacemakers are described in U.S. Pat. Nos. 4,424,551 and 5,333,095, the contents of which are incorporated herein. These types of single pole coaxial feedthrough filter capacitors are very small in size and very effective in attenuating EM signals in the frequency range from 8 MHz to 10 GHz. This frequency range includes cellular phones and many other sources of EMI. However, this type of filter when used alone is ineffective for attenuating EMI at very low frequencies (from DC to 8 MHz), such as the powerful EM field that is produced by certain electronic article surveillance (EAS) systems.

EAS systems are widely used throughout the world to deter theft in retail stores by detecting a tag or sensor placed on an article (for example a shirt or pair of shoes). Unless the tag is removed or degaussed, the sensing field will set off an alarm if the thief attempts to leave the retail store. EAS systems are produced by various manufacturers and typically operate from 73 Hz to 10 GHz. EAS systems operating at frequencies above 8 MHz in general do not interfere with cardiac pacemakers or implantable cardioverter defibrillators (ICDs). This is due to the effectiveness of the broadband type EMI filters described above in combination with substrate mounted chip capacitors inside of the medical device housing. However, most EAS systems in the United States operate at frequencies below 8 MHz because these tend to be the most effective at deterring theft (higher frequency EAS systems are easily defeated by a thief lining his or her handbag with aluminum foil or like shielding). The most widely used EAS system in the United States is manufactured by Sensormatic Inc. under the model name "Ultramax", and employs a 58 KHz EM sensing field which is produced between two pedestals and has a strong magnetic component. There are also EAS systems operating at 68 KHz and 39.5 KHz.

The Sensormatic Ultramax 58 KHz EM field is burst modulated at a rate of approximately 60 Hertz. This is problematic in that human cardiac activity occurs in the frequency range from 10 Hz to 100 Hz. Accordingly, the sensing/monitoring circuits of pacemakers and ICDs are designed to detect cardiac signals in this frequency range. The 58 KHz EAS carrier signal can enter the pacemaker housing and input circuitry via the cardiac leads or pacemaker telemetry coils. Pacemaker and ICD circuitry contain non-linear circuit elements such as high-voltage protection diodes which can act as modulation detectors (like a single sideband detector). After the 58 KHz carrier encounters a non-linear circuit element, the detected 60 Hz modulation can then enter past the pacemaker band pass filters (which pass signals between 10 and 100 Hz) and be amplified. The pacemaker can then confuse the EAS modulation as cardiac electrical activity. In the worst case, the pacemaker may inhibit or skip beats because it confuses the EAS modulation for normal cardiac activity (a demand pacemaker inhibits or shuts off in the presence of a normal heart beat).

In a paper presented at the annual meeting of the North American Society of Pacing and Electrophysiology (NASPE), 1997, New Orleans, Dr. McGiver presented a paper which reported on numerous interactions between pacemakers and EAS devices. In addition, the FDA has also received a number of Medical Device Reports (MDRs) which report on interaction between pacemakers and EAS systems.

One approach to public safety would be to warn pacemaker wearers to walk quickly between or avoid loitering near EAS pedestals (some pacemaker patient manuals warn patients to exit quickly through the center of the pedestals). However, some of the latest architectural model EAS systems are designed to be placed out-of-sight under a floor or in cabinetry. Other counter top systems may be placed next to checkout lines. Warning pacemaker wearers to avoid retail stores is, of course, unrealistic and would create much patient anxiety. This is particularly true for the elderly (of whom many wear pacemakers) where shopping is an important recreational activity. Yet another approach would be to place warning signs in the front of stores with low frequency EAS systems. This too, however, would create anxiety and deter the elderly from an important facet of daily living.

Removal of EAS systems from retail stores is equally unacceptable. Retail theft is a major financial burden on society. EAS systems perform a vital role in keeping the costs of goods reasonable while allowing the public unimpeded access to retail stores.

Usually, management of EMI at low frequencies such as 58 KHz is accomplished by the twisting of lead wire pairs.

In non-human implant electronic systems, twisting of lead wires is a common practice to cancel EMI currents that are induced due to EM fields. However, the lead systems used for human implant have not been designed with field cancellation as an aim. Designing new twisted lead systems for human implant is problematic due to technical challenges and the many years of redesign and subsequent reliability testing that would be required. For example, cardiac implant leads must withstand the rigors of millions of heart beat muscle contractions.

Accordingly, there is a need for an improved EMI filter designed specifically to protect pacemakers or ICDs from EAS systems. Such an EMI filter must be very small and lightweight to fit inside of an implantable medical device, and must not attenuate adjacent pacemakers/ICD telemetry signals or minute ventilation (MV) signals. These normal pacemaker operating signals are typically close in frequency to the EAS 58 KHz system with pacemaker telemetry examples including 75 KHz and 100 KHz. This close frequency spacing generally precludes the use of broadband filters. Further, such a novel EMI filter must have a form factor which readily will fit inside of the housing of a pacemaker or ICD, and must be highly reliable but reasonable in cost. Additionally, such an EMI filter must be placed very close to the point of entry of the EAS signal into the pacemaker/ICD circuitry. It is very important to bypass or reject the EAS carrier before it is detected. Once the EAS signal encounters a non-linear circuit element, its 60 Hz modulation will be detected. Once detected, it is simply not practical to filter the modulation as this is a frequency which the implantable medical device monitors as normal cardiac activity. Finally, such a filter is needed which is capable of both common and differential mode rejection. This need varies with the design of the implantable medical device and placement/design of the implant lead wires. The present invention fulfills these needs and provides other related advantages.

SUMMARY OF THE INVENTION

The present invention resides in a novel electromagnetic interference (EMI) filter that is designed to attenuate one or more specific frequencies in order to provide electromagnetic capability of an electronic device while in the presence of an electromagnetic emitter operating at the same or similar frequencies. The EMI filter comprises, generally, a broadband electromagnetic interference filter associated with one or more leads of an electronic device and capable of attenuating a range of frequencies, and an inductor-capacitor (L-C) series resonant notch electromagnetic interference filter associated with the leads of the electronic device and capable of attenuating a specific frequency outside the attenuation range of the broadband EMI filter. This combined notch and low pass filter arrangement is particularly effective in an implantable medical device such as a cardiac pacemaker or an implantable cardioverter defibrillator (ICD) against passage of external interference signals, such as those caused by digital cellular phones and electronic article surveillance systems operating at low frequencies.

More specifically, the broadband EMI filter typically comprises a capacitive low pass filter such as a feedthrough filter capacitor which forms at least a portion of a hermetic terminal for an implantable medical electronic device. In various embodiments of the invention, the notch EMI filter comprises an L-C series resonant circuit disposed between each lead of the electronic device and a ground and/or between two leads of the electronic device. Further, the notch EMI filter may comprise paired L-C series resonant circuits such that the respective value of the inductor and the capacitor elements are reversed in order to provide both common mode and differential mode attenuation. Moreover, the notch EMI filter may comprise a plurality of notch electromagnetic interference filters associated with the leads of the electronic device and which are capable of attenuating a plurality of specific frequencies outside the attenuation range of the broadband EMI filter.

In another preferred form of the invention, a capacitive element of the notch EMI filter is integrated with the feedthrough filter capacitor. In this case the EMI filter includes a casing of dielectric material through which the leads of the electronic device extend. A first set of electrode plates is disposed within the casing in conductive relation with the leads of the electronic device. A second set of electrode plates is also disposed within the casing in non-conductive relation with the leads of the electronic device and in an alternating stack with the first set of electrode plates. A first conductive termination surface is conductively coupled to the second set of electrode plates. The first and second sets of electrode plates form the broadband EMI filter. Further, a third set of electrode plates is disposed within the casing in conductive relation with the leads of the electronic device. A fourth set of electrode plates is disposed within the casing in non-conductive relation with the leads of the electronic device and in an alternating stack with the third set of electrode plates. A second conductive termination surface is conductively coupled to the fourth set of electrode plates, wherein the third and fourth sets of electrode plates form the capacitive element of the notch EMI filter. Finally, an inductor is conductively coupled to the second conductive termination surface to form an inductive element of the notch EMI filter.

The inductor may be conductively coupled to the first conductive termination surface or between the second conductive termination surfaces of two leads of the electronic device. The inductor may comprise a chip inductor or a wound wire solenoid on a ferrite core of toroidal wound wire construction. The second conductive termination surface may be disposed in through-holes within the dielectric casing, or may comprise a metalized pad on an exterior surface of the dielectric casing.

The present invention further resides in a process for providing electromagnetic capability of an electronic device while in the presence of an electromagnetic emitter operating at the same or a similar frequency or frequencies. In a preferred form of the invention, the process provides electromagnetic compatibility of an implantable electronic medical device while in the presence of an electronic article surveillance (EAS) device operating at the same or a similar frequency or frequencies. In this case, the process steps include (1) associating a low pass broadband electromagnetic interference (EMI) filter with one or more leads of the implantable electronic medical device, and (2) attenuating one or more specific frequencies passing through the feedthrough filter capacitor and genera ted by the EAS device utilizing a notch electromagnetic interference (EMI) filter. Preferably, the broadband EMI filter comprises a feedthrough filter capacitor that forms at least a portion of a hermetic terminal for the implantable medical electronic device.

The novel EMI filter of the present invention is, thus, very small and lightweight so as to fit in side the implantable medical device, highly reliable, capable of both common and differential mode reject ion, an d may be placed very close to the point of entry of the EAS signal into the implantable medical device circuitry.

Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIGS. 1A–1D illustrate a prior art quadpolar coaxial feedthrough filter capacitor, wherein FIG. 1A is a perspective view thereof, FIG. 1B illustrates the lay up pattern for ground electrode plates within the capacitor, FIG. 1C illustrates the lay up pattern for four sets of active electrode plates within the capacitor, and FIG. 1D is an electrical schematic;

FIGS. 2A–2D illustrate a prior art rectangular bipolar feedthrough filter capacitor, wherein FIG. 2A is a perspective view thereof, FIG. 2B shows the lay up pattern for a set of ground electrode plates within the capacitor, FIG. 2C shows the lay up pattern for two sets of active electrode plates within the capacitor, and FIG. 2D is an electrical schematic;

FIGS. 4A and 4B illustrate a series resonant notch filter, wherein FIG. 4A is a schematic circuit diagram for a notch filter in an electronic article surveillance (EAS) system operating at 58 KHz, and FIG. 4B gives the formula for the resonant frequency of the notch filter;

FIGS. 12A–12G illustrate a bipolar feedthrough filter capacitor similar to that shown in FIG. 2, but having two integrated capacitors in accordance with the invention in a co-planar relationship, wherein FIG. 12A is a perspective and partially sectional view of the integrated bipolar feedthrough capacitor, FIG. 12B illustrates the lay up pattern for ground electrode plates of a notch EMI filter element, FIG. 12C shows the lay up pattern for active electrode plates for the notch EMI filter element, FIG. 12D shows the lay up pattern for active electrode plates for the broadband EMI filter element, FIG. 12E shows the lay up pattern for a set of ground electrode plates for the broadband EMI filter, FIG. 12F is a perspective view of the capacitor of FIGS. 12A–12E having a pair of terminal pins extending therethrough, and FIG. 12G is an electrical schematic of the feedthrough filter capacitor assembly of FIG. 12F;

FIG. 13A is a perspective view of the feedthrough filter capacitor assembly of FIG. 12F combined with a discreet inductor element in accordance with the invention;

FIG. 13B is an electrical schematic of the feedthrough filter capacitor assembly of FIG. 13A;

FIGS. 14A–14E show another bipolar feedthrough filter capacitor similar to that illustrated in FIGS. 12A–12E and further having a discreet inductor element attached at through-holes in the capacitor, wherein FIG. 14A is a perspective view of the integrated bipolar feedthrough capacitor, FIG. 14B illustrates the lay up pattern for ground electrode plates of a notch EMI filter element, FIG. 14C shows the lay up pattern for active electrode plates for the notch EMI filter element, FIG. 14D shows the lay up pattern for active electrode plates for the broadband EMI filter element, and FIG. 14E shows the lay up pattern for a set of ground electrode plates for the broadband EMI filter;

FIGS. 15A–15E illustrate yet another bipolar feedthrough filter capacitor similar to FIGS. 14A–14E and having a chip inductor electrically connected between two notch EMI filter capacitors, wherein FIG. 15A is a perspective view of the integrated bipolar feedthrough capacitor, FIG. 15B illustrates the lay up pattern for ground electrode plates of a notch EMI filter element, FIG. 15C shows the lay up pattern for active electrode plates for the notch EMI filter element, FIG. 15D shows the lay up pattern for active electrode plates for the broadband EMI filter element, and FIG. 15E shows the lay up pattern for a set of ground electrode plates for the broadband EMI filter;

FIGS. 16A–16E show an integrated quadpolar feedthrough filter capacitor of an implantable defibrillator having two sensing leads with notch filtering utilizing a toroidal inductor, wherein FIG. 16A is a perspective view of the integrated quadpolar feedthrough capacitor, FIG. 16B illustrates the lay up pattern for ground electrode plates of a notch EMI filter element, FIG. 16C shows the lay up pattern for active electrode plates for the notch EMI filter element, FIG. 16D shows the lay up pattern for active electrode plates for the broadband EMI filter element, and FIG. 16E shows the lay up pattern for a set of ground electrode plates for the broadband EMI filter;

FIGS. 17A–17F illustrate dual line-to-ground notch EMI filters mounted on an integrated bipolar feedthrough capacitor, wherein FIG. 17A is a perspective view of the integrated bipolar feedthrough capacitor, FIG. 17B is an electrical schematic thereof, FIG. 17C illustrates the lay up pattern for ground electrode plates of a notch EMI filter element, FIG. 17D shows the lay up pattern for active electrode plates for the notch EMI filter element, FIG. 17E shows the lay up pattern for active electrode plates for the broadband EMI filter element, and FIG. 17F shows the lay up pattern for a set of ground electrode plates for the broadband EMI filter; and FIGS. 18A–18F illustrate a quadpolar feedthrough filter capacitor with line-to-ground chip inductors, wherein FIG.

18A is a perspective view thereof, FIG. 18B is an electrical schematic thereof, FIG. 18C illustrates the lay up pattern for ground electrode plates of a notch EMI filter element, FIG. 18D shows the lay up pattern for active electrode plates for the notch EMI filter element, FIG. 18E shows the lay up pattern for active electrode plates for the broadband EMI filter element, and FIG. 18F shows the lay up pattern for a set of ground electrode plates for the broadband EMI filter.

DETAILED DESCRIPTION OF THE PREFERRED EMBODIMENTS

Figure 12A:
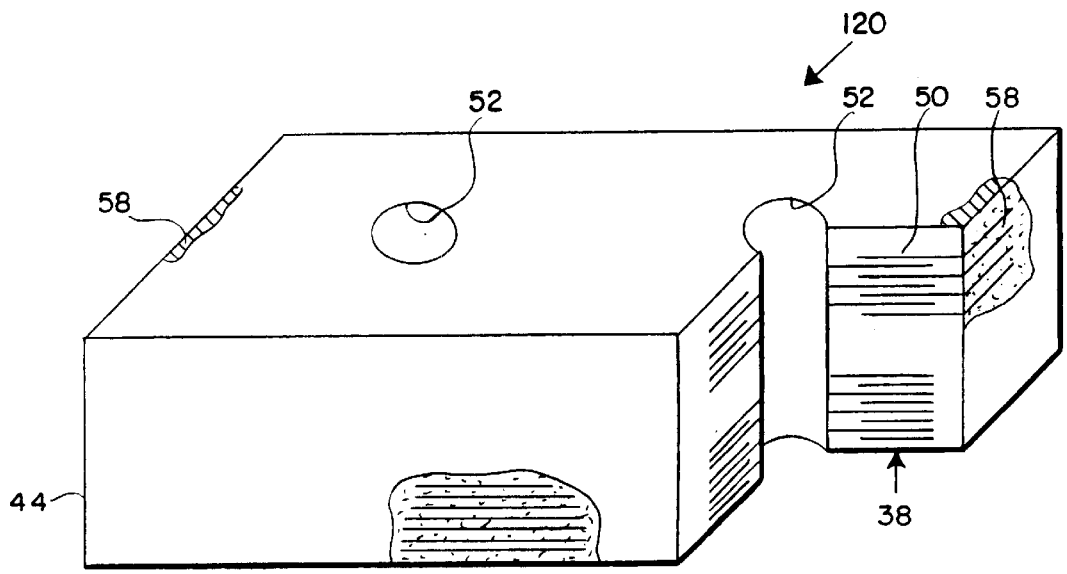

As shown in the drawings for purposes of illustration, the present invention is concerned with a novel electromagnetic interference (EMI) filter that is designed to attenuate one or more specific frequencies in order to provide electromagnetic capability of an electronic device while in the presence of an electromagnetic emitter operating at the same or similar frequencies. The novel EMI filter of the present invention is designated generally by the reference number 20 in FIGS. 5–7 and 9A, by the reference number 120 in FIGS. 12A, 12F and 13A, by the reference number 220 in FIG. 14A, by the reference number 320 in FIG. 15A, by the reference number 420 in FIG. 16A, by the reference number 520 in FIG. 17A and by the reference number 620 in FIG. 18A. In the following description, functionally equivalent elements of the various embodiments will share the same reference number. The novel EMI filter 20-620 of the present invention includes a novel integrated notch EMI filter 22 which is combined with a broadband lowpass EMI filter 24, and related methods of construction, particularly of the type used in implantable medical devices such as cardiac pacemakers, ICDs and the like, to decouple and shield undesirable electromagnetic interference (EMI) signals from the device. More specifically, this invention relates to protecting electronic devices from the EM fields of single frequency emitters which operate outside the frequency range of a broadband low pass filter.

In one preferred form of the invention, the notch EMI filter 22 is integrated with a hermetic feedthrough terminal pin and ceramic feedthrough capacitor (low pass filter) assembly 26. Said assembly 26 may contain one or more coaxial filter capacitors forming the broadband low pass EMI filter 24, and is adapted particularly for use in connecting a lead wire or electrode 28 through a hermetically sealed housing 30 to internal electronic components 32 of the medical device while decoupling EMI against entry into the sealed housing. The invention is also suited to decoupling signals that are directly induced on a telemetry coil or the like. This invention is particularly designed for use in cardiac pacemakers (bradycardia devices), cardioverter defibrillators (tachycardia devices) and combined pacemaker/defibrillator devices. This invention is also applicable to a wide range of other EMI filter applications, such as neurostimulators, cochlear implants and the like.

When combined in the manner described herein, the notch EMI filter 22 can effectively attenuate the electromagnetic field of a powerful low frequency emitter which is outside the effective attenuation frequency range of the broadband low pass EMI filter 24. On the other hand, the broadband low pass EMI filter 24 is effective at filtering a broad range of higher frequencies (such as cellular phones).

In another form of the invention, the notch EMI filter 22 is integrated in a co-planar relationship with a ceramic feedthrough capacitor assembly 26. This assembly is suitable for the mounting of the required inductor element(s) 34. As described herein, the inductors 34 may be of many types including surface mount chip, ferrite core, wound, and the like.

The invention is particularly suitable for co-installation with the broadband low pass EMI filters 24 described in U.S. Pat. No. 5,571,539, the contents of which are incorporated herein. For example, the isolated ground capacitor of U.S. Pat. No. 5,571,539 allows for a great deal of differential mode rejection while not overly suppressing the RF signals required for pacemaker minute ventilation circuitry.

The novel notch EMI filter 22 consists of a series inductor 34 and capacitor 36 elements that are designed to resonate at the particular frequency of an electromagnetic emitter, such as an electronic article surveillance (EAS) system. It is well known in the art that at resonance a capacitive reactance in series with an inductive reactance are equal and opposite in sign and cancel to zero in the imaginary plane ($+jXc=-jXL$). Accordingly, the impedance of such a series combination in resonance is resistive (the resistance is due to connecting wire, the wire in the inductor and the equivalent series resistance (ESR) of the capacitor 36).

As illustrated in FIGS. 1a–1d and FIGS. 2a–2d, in a typical broadband low pass EMI filter 24 construction (as described in greater detail in U.S. Pat. No. 5,333,095), a coaxial ceramic feedthrough filter capacitor 38 is used in a feedthrough capacitor assembly 26 to suppress and decouple undesired interference or noise transmission along a terminal pin 28, and may comprise a so-called discoidal capacitor having two sets of electrode plates 40 and 42 embedded in spaced relation within an insulative dielectric substrate or base 44, formed typically as a ceramic monolithic structure. One set of the electrode plates 40 is electrically connected at an inner diameter cylindrical surface of the discoidal capacitor structure to the conductive terminal pin 28 utilized to pass the desired electrical signal or signals. The other or second set of electrode plates 42 is coupled at an outer diameter surface of the discoidal capacitor to a cylindrical ferrule 46 of conductive material, wherein the ferrule is electrically connected in turn to the conductive housing of the electronic device. The number and dielectric thickness spacing of the electrode plate sets varies in accordance with the capacitance value and the voltage rating of the discoidal capacitor 38. In operation, the discoidal capacitor 38 permits passage of relatively low frequency electrical signals along the terminal pins 28, while shielding and decoupling/attenuating undesired interference signals of typically high frequency to the conductive housing. Feedthrough capacitors 38 of this general type are available in unipolar (one), bipolar (two), tripolar (three), quadpolar (four), pentapolar (five), hexpolar (six) and additional lead configurations. The feedthrough capacitors 38 of this general type are commonly employed in implantable cardiac pacemakers and defibrillators and the like, wherein the pacemaker housing is constructed from a biocompatible metal, such as titanium alloy which is electrically coupled to the feedthrough filter capacitor. As a result, the filter capacitor and terminal pin assembly 26 prevents entrance of interference signals to the interior of the pacemaker housing, wherein such interference signals could otherwise adversely affect the desired cardiac pacing or defibrillation function.

Figure 1A:
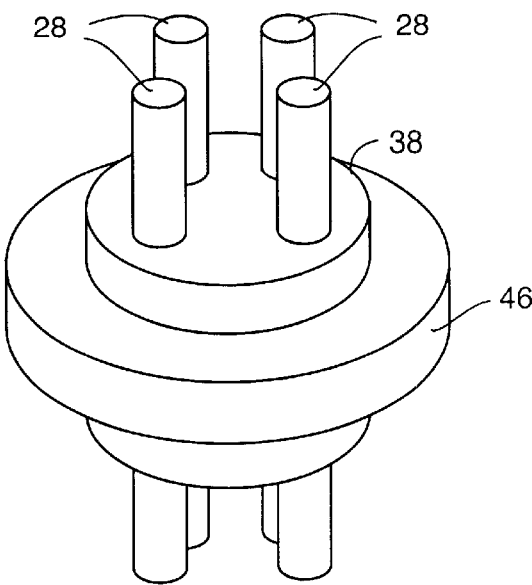
Figure 1D:
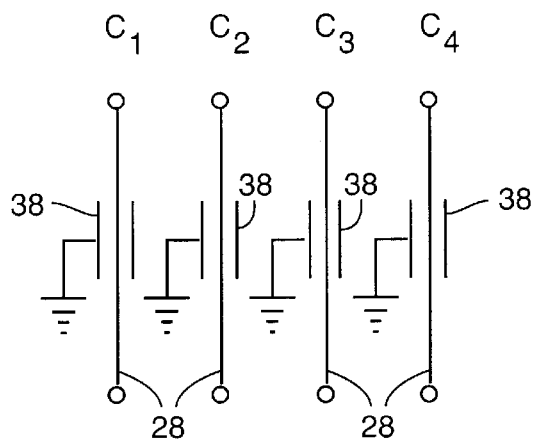
Figure 1B:
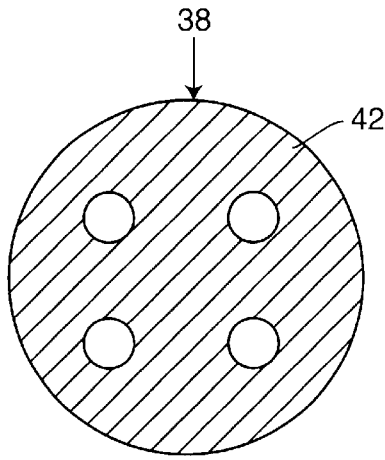
Figure 1C:
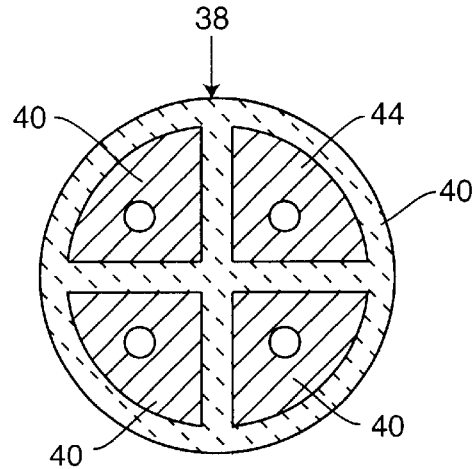

With the foregoing in mind, FIGS. 1A–1D illustrate a prior art round quadpolar coaxial feedthrough capacitor 38 mounted to the hermetic terminal 46 of a cardiac pacemaker in accordance with U.S. Pat. No. 5,333,095. The electrical schematic and internal electrode plates are shown in FIGS. 1B–1D.

Figure 2A:
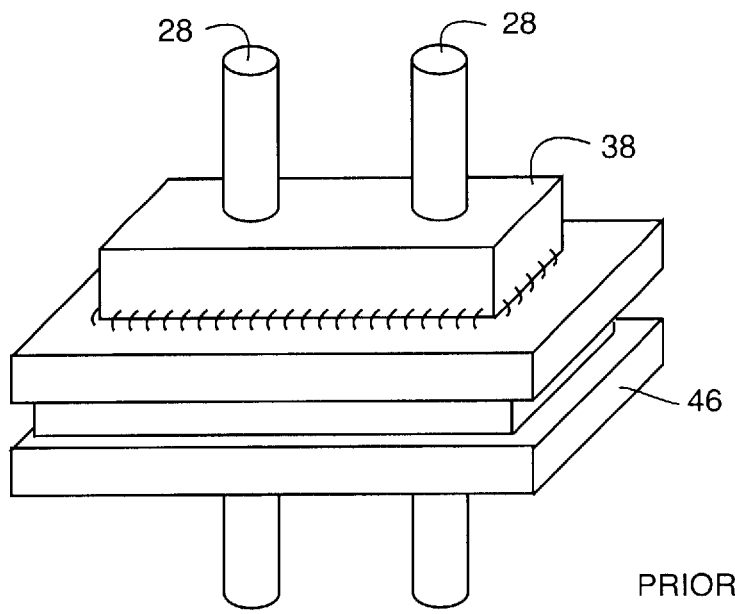
Figure 2B:
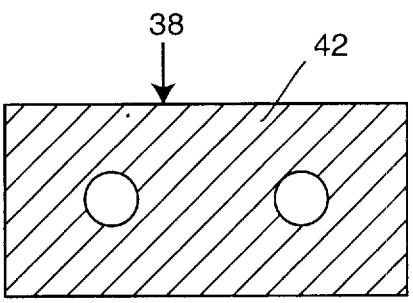
Figure 2C:
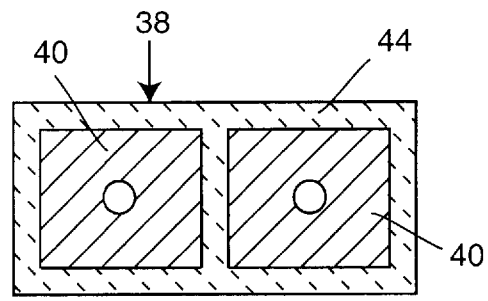
Figure 2D:
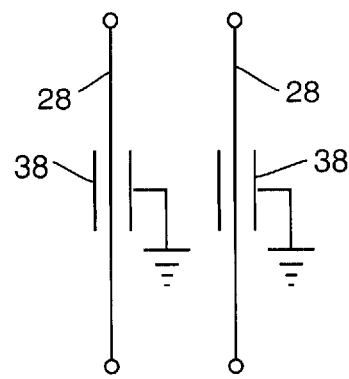

FIGS. 2A–2D illustrate a prior art rectangular bipolar feedthrough capacitor 38 mounted to the hermetic terminal 46 of a cardiac pacemaker in accordance with U.S. Pat. No. 5,333,095. The electrical schematic and internal electrode plates are shown in FIGS. 2B–2D.

Figure 3:
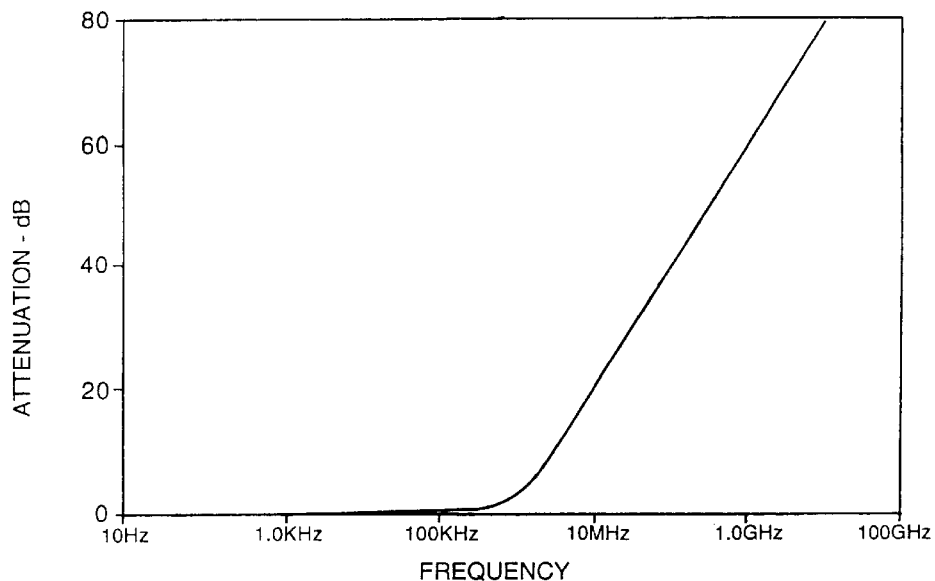
FIG. 3 is a graph illustrating an exemplary attenuation characteristic curve of prior art feedthrough filter capacitors such as those illustrated in FIGS. 1 and 2.

FIG. 3 is a graph which illustrates the attenuation characteristic curve of the prior art feedthrough capacitor EMI filters 38 of FIGS. 1 and 2.

Figure 4A:
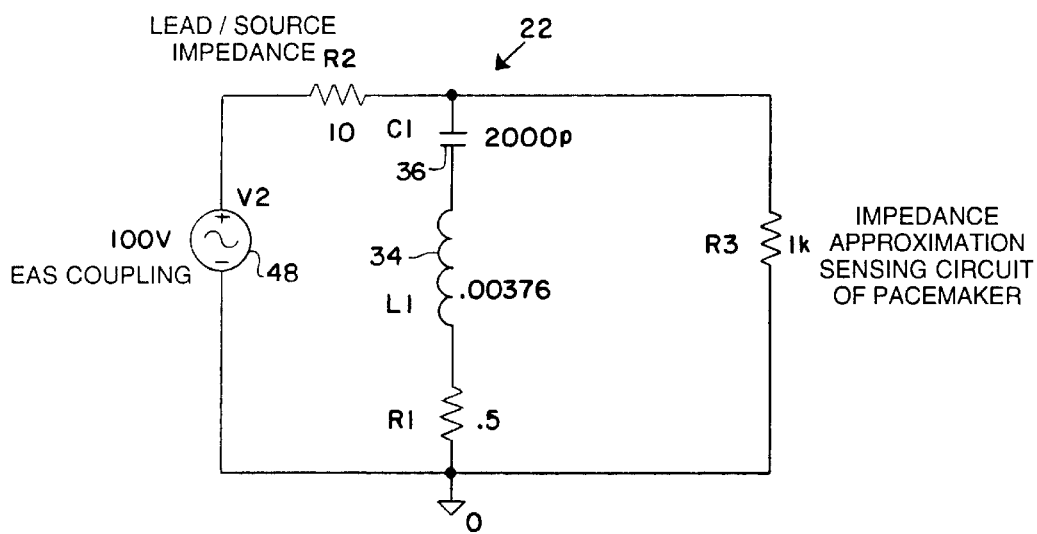
Figure 4B:
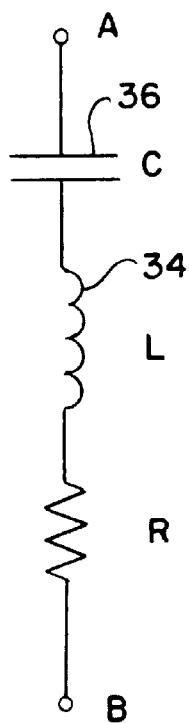

FIGS. 4A and 4B illustrate the basic series resonant notch EMI filter 22 element of the present invention. FIG. 4A is a schematic circuit diagram for a notch EMI filter 22 designed for an EAS system operating at 58 KHz. FIG. 4B gives the formula for the resonant frequency.

Figure 5:
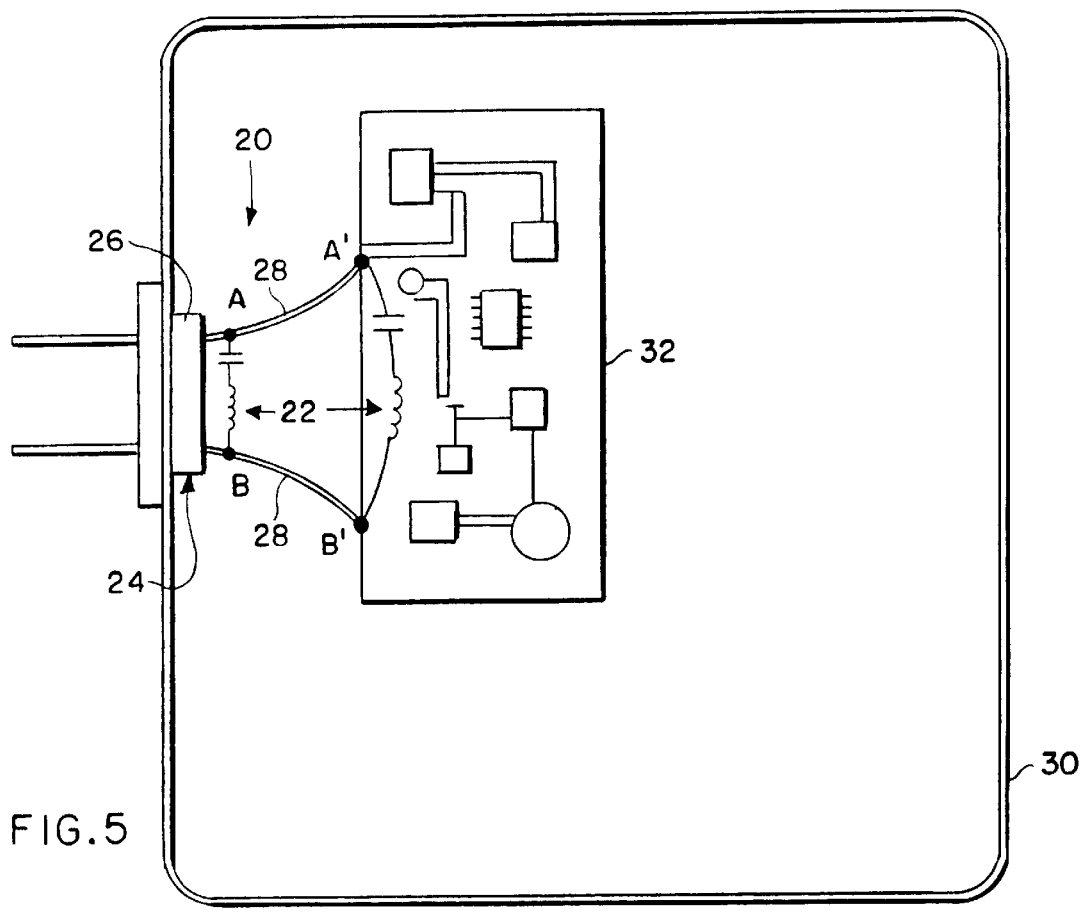
FIG. 5 is a schematic illustration of an exemplary cardiac pacemaker or implantable defibrillator, showing line-to-line placement of a notch filter to decouple an EAS signal before it can encounter a non-linear circuit element (two primary locations for the notch filter are illustrated)

FIG. 5 illustrates the internal circuitry of a cardiac pacemaker or implantable defibrillator showing a line to line placement of the notch EMI filter 22 element to decouple the EAS signal before it can encounter a non-linear circuit element (modulation detector). A–B shows the preferred location (very close to the EMI feedthrough filter/hermetic terminal 26), within a metallic housing 30. A'–B' illustrates an acceptable substrate mounted location provided that there are no non-linear circuit elements (such as protection diodes) between A'–B' and the point of lead ingress. The line to line placement of the notch filter 22 is in order to decouple an EAS signal that is differential mode between the two sensing lead wires 28.

Figure 6:
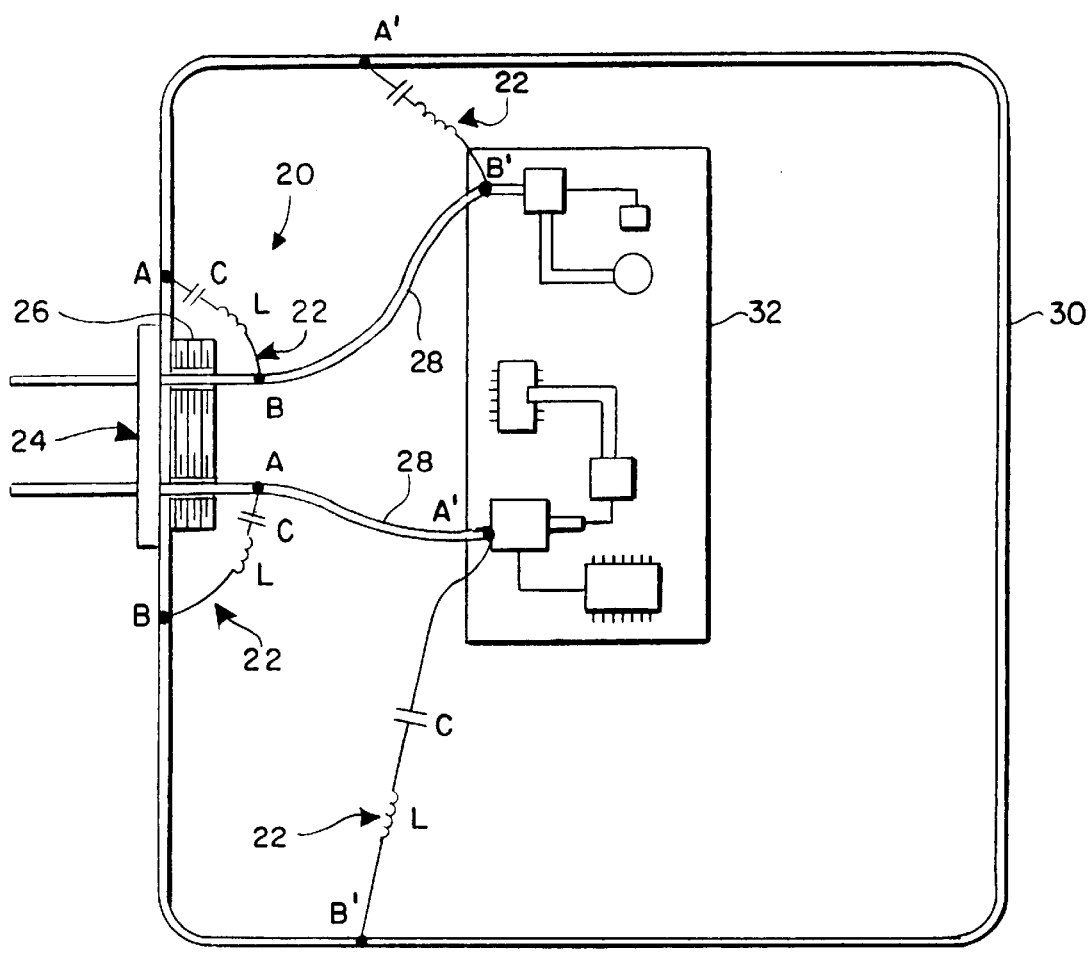
FIG. 6 is a schematic illustration similar to that of FIG. 5, showing line-to-ground (shield) placements of notch filters to decouple the EAS signal before it can encounter a non-linear circuit element (with alternate preferred locations of the notch filters also being shown)

FIG. 6 illustrates the internal circuitry of a cardiac pacemaker or implantable defibrillator showing line to ground (shield) placements of the notch EMI filter elements 22 to decouple the EAS signal before it can encounter a non-linear circuit element (modulation detector). A–B shows the preferred location (very close to the EMI feedthrough filter/ hermetic terminal 26). A'–B' illustrates an acceptable alternate substrate mounted provided that there are no non-linear circuit elements (such as protection diodes) between A'–B' and the point of lead ingress. The line to ground/shield placement of the notch EMI filter 22 is in order to decouple an EAS signal that is common mode between either or both of the two sensing lead wires 28 with reference to the shield 30 (RF ground).

Figure 7:
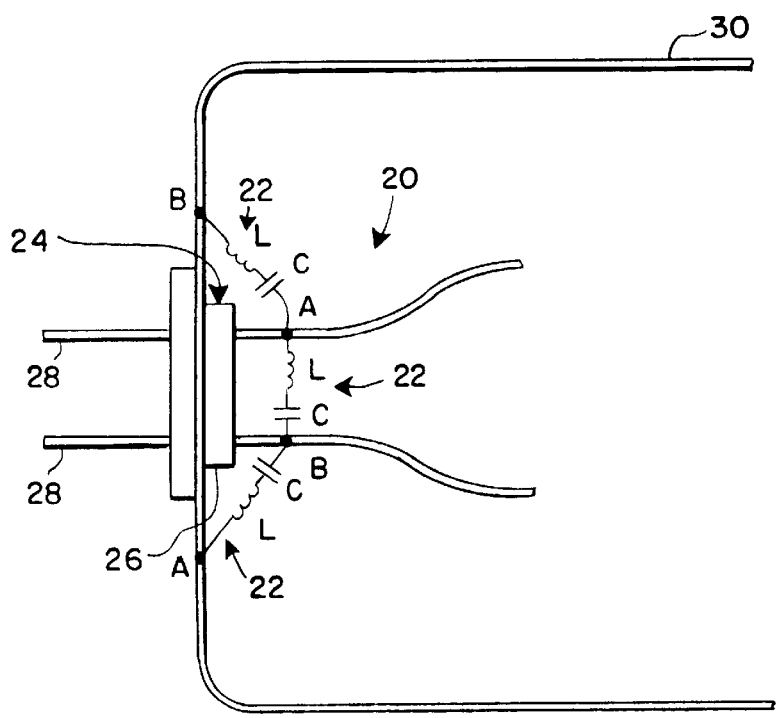
FIG. 7 is a schematic illustration similar to FIGS. 5 and 6, showing notch EMI filters connected both line-to-line and line-to-ground.

FIG. 7 combines FIGS. 5 and 6 with the notch EMI filter 22 connected both line to line and line to ground. This is to provide protection to both common and differential mode EAS signals.

Figure 8A:
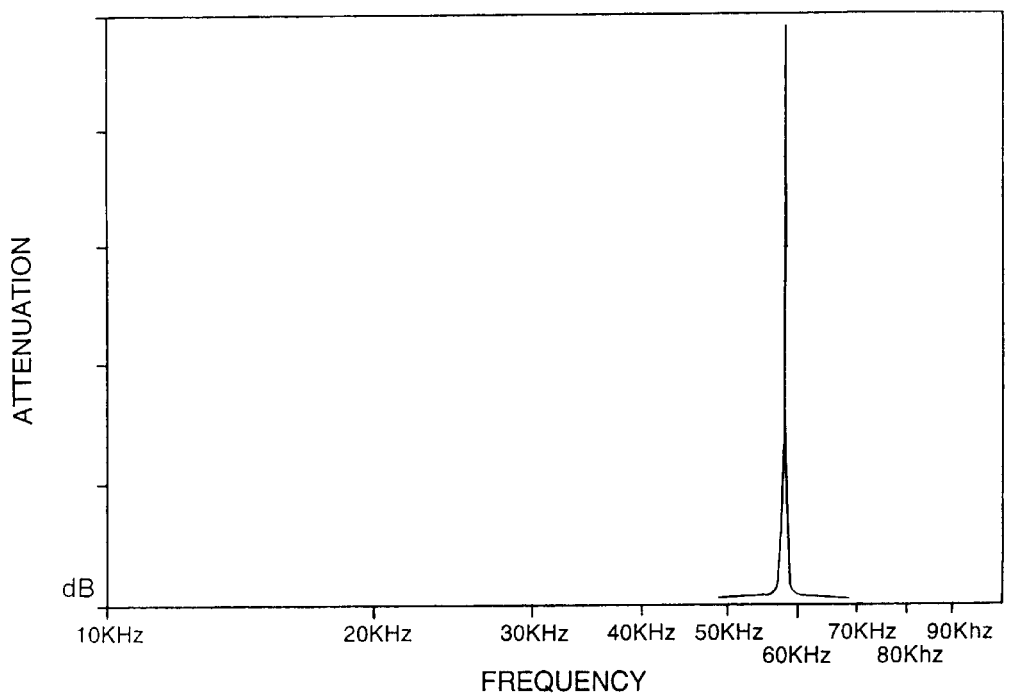
FIGS. 8A and 8B are graphs which illustrate the attenuation characteristic verses frequency for the notch EMI filters of FIGS. 5 and 6.
Figure 8B:
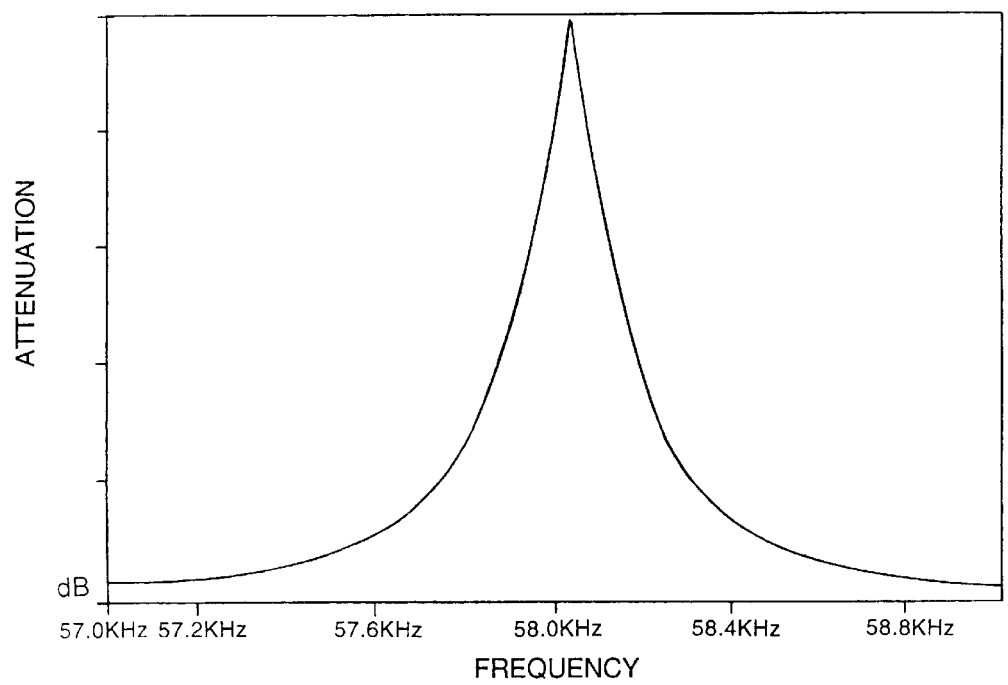

FIGS. 8A and 8B are graphs which illustrate the attenuation characteristic versus frequency for the notch EMI filters 22 of FIGS. 5 and 6.

Figure 9A:
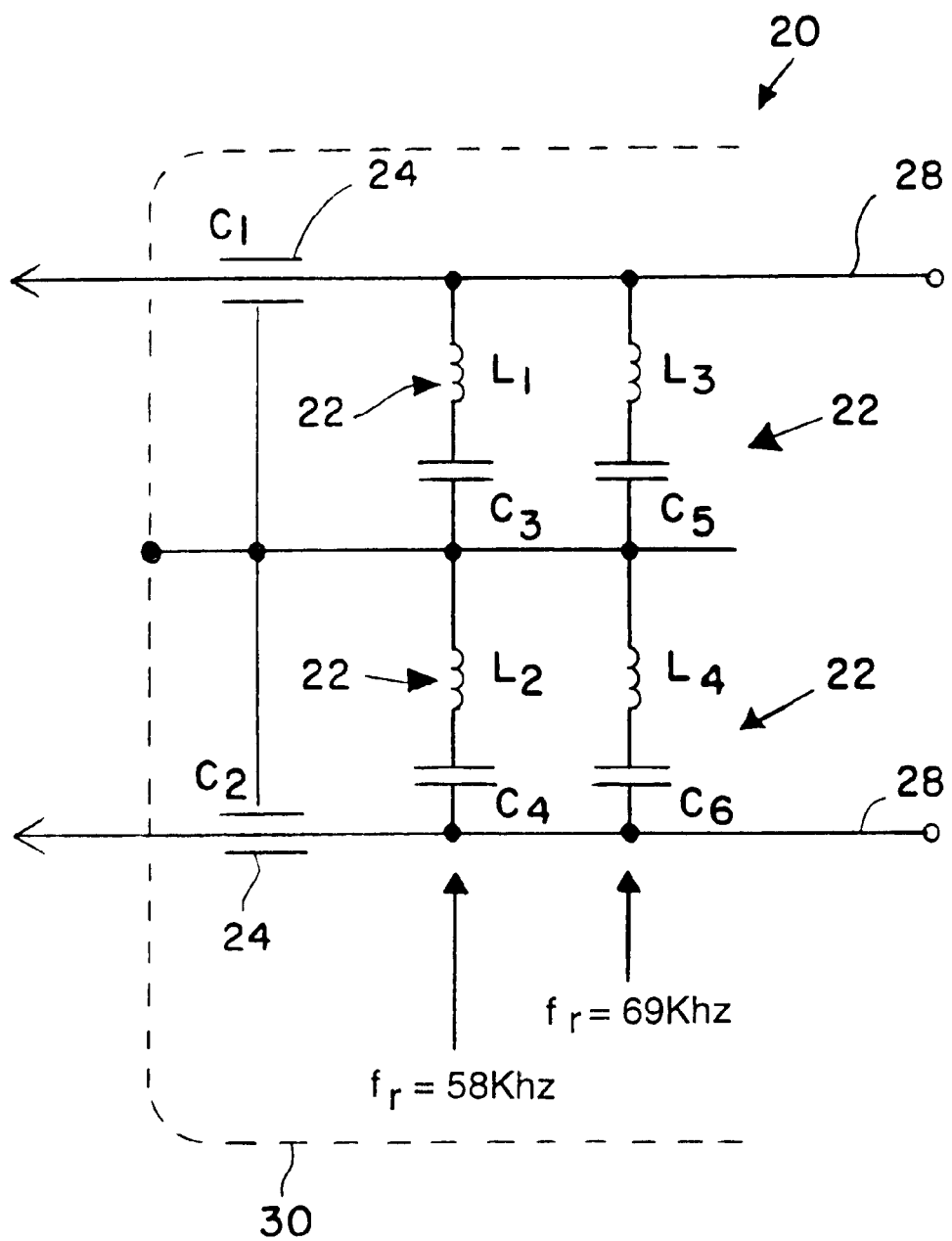
FIGS. 9A and 9B illustrate the use of multiple notch EMI filters to attenuate a corresponding number of specific frequencies.
Figure 9B:
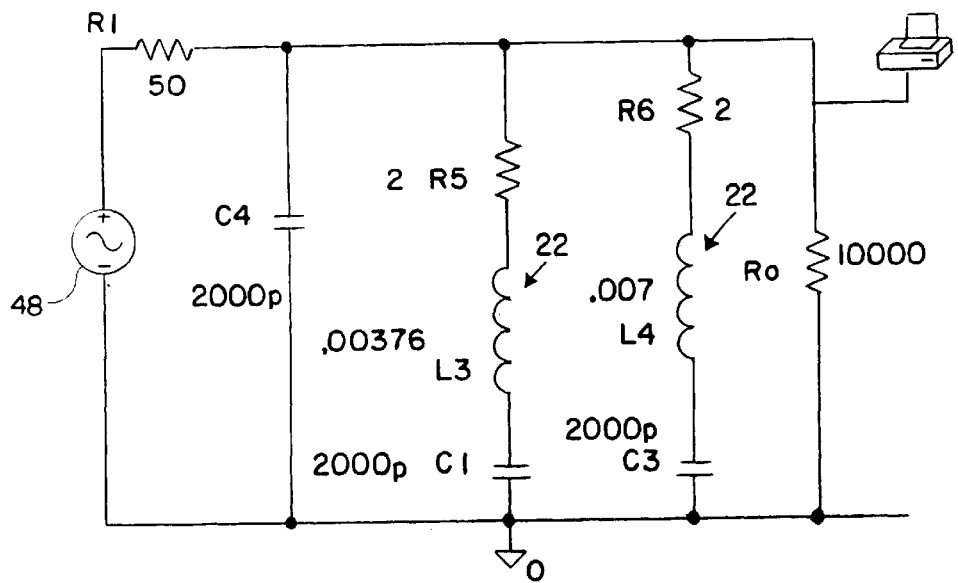

FIGS. 9A and 9B illustrate multiple notch EMI filter elements 22 in parallel and tuned to 58 KHz and 69 KHz. As illustrated, $L_1$ and $C_3$, and $L_2$ and $C_4$ resonate at 58 KHz. $L_3$ and $C_5$, and $L_4$ and $C_6$ resonate at 69 KHz. $C_1$ and $C_2$ represent prior art broadband low pass EMI filters 24, 38. In a preferred embodiment $L_1=C_4$, $C_3=L_2$, $L_3=C_6$, and $C_5=L_4$. In FIG. 9B the reference number 48 schematically represents a source of electromagnetic interference, or an electronic article surveillance (EAS) device 48.

Figure 10:
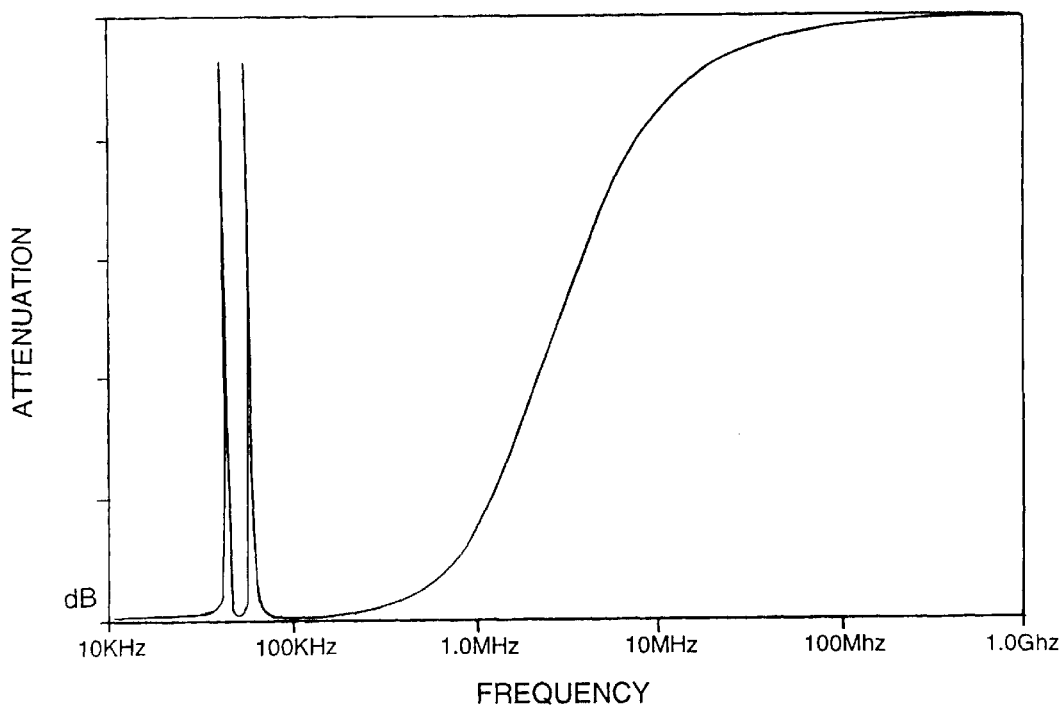
FIG. 10 is a graph which illustrates the attenuation characteristics of the two parallel notch EMI filters of FIGS. 9A and 9B combined with a typical broadband low pass filter, such as those illustrated in FIGS. 1 and 2.

FIG. 10 is a graph which illustrates the attenuation characteristics of the two parallel notch EMI filters 22 of FIGS. 9A and 9B combined with the broadband lowpass EMI filter 24 of FIGS. 1 or 2. The first spike represents attenuation at 58 KHz, and the second spike represents attenuation 69 KHz.

Figure 11:
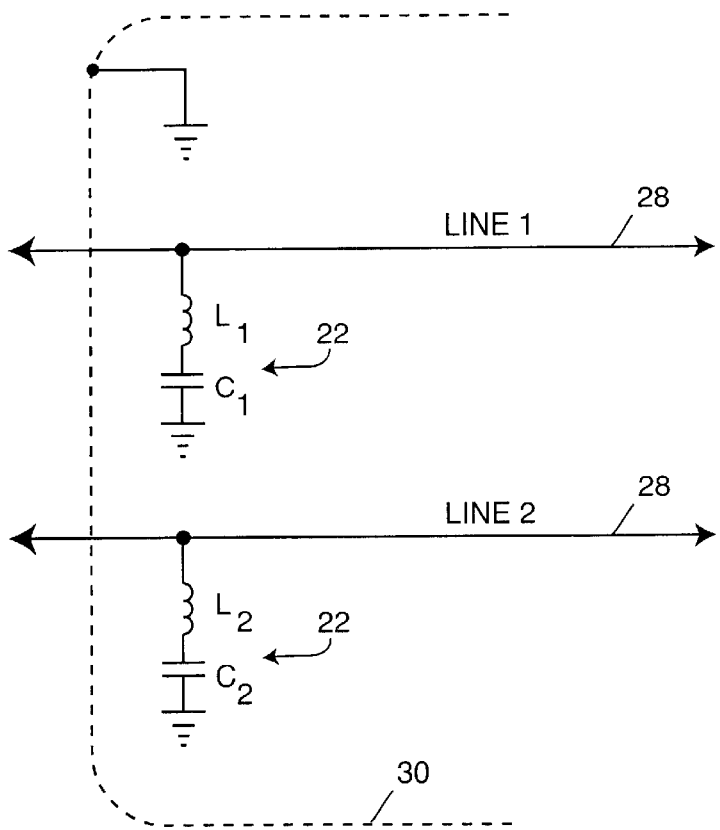
FIG. 11 is a schematic illustration showing a pair of notch EMI filters connected from lead-to-ground with the L and C values reversed, and further illustrating mathematical formulas which show that reversing the L and C values causes a resonant frequency to be the same for line-to-ground (common mode) and also lead-to-lead (differential mode) notch filter placement.

FIG. 11 illustrates a pair of notch EMI filters 22 connected from lead 28 to ground with the L and C values reversed. Reversing the L and C values causes the resonant frequency to be the same on either line to ground (common mode) and also from lead to lead (differential mode). The mathematical relationship is derived which shows this effect.

In accordance with the invention, the coaxial filter capacitor 38 described above may be integrated in a novel coplanar relationship with isolated internal capacitors 50 which form the capacitive element(s) 36 of the notch EMI filter 22 portion.

The invention is also suited to conventional hybrid circuit manufacturing techniques. For example, the capacitor 26 of the notch EMI filter 22 may be laid down directly on the surface of a hermetic terminal, the broadband feedthrough capacitor or on a circuit substrate such as alumina. Many alternative mounting and installations methods will be obvious to those skilled in the art.

Figure 12B:
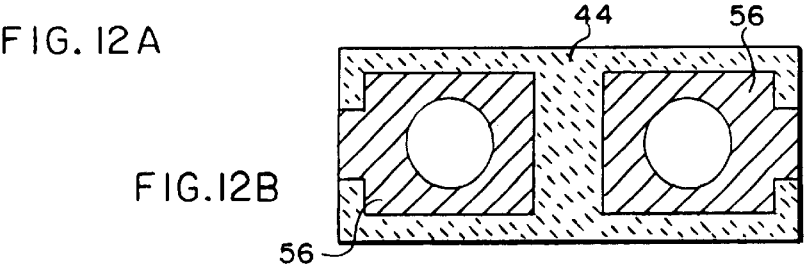
Figure 12C:
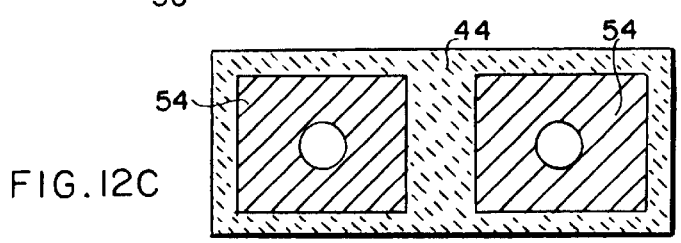
Figure 12D:
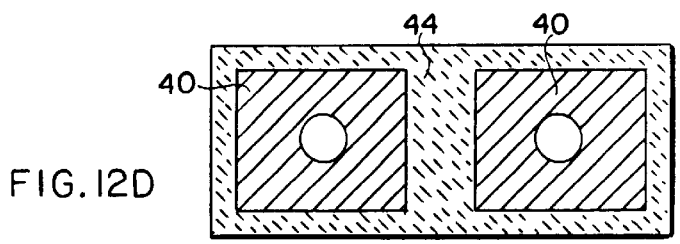
Figure 12E:
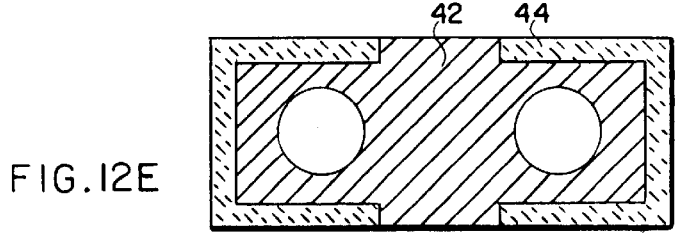

FIGS. 12A–12E show a bipolar feedthrough capacitor similar to FIG. 2, but having two integrated capacitors 38 and 50 in accordance with the invention in a co-planar relationship. FIGS. 12B and 12C show the electrode plate patterns for the notch filter capacitors 50 in accordance with the invention. FIGS. 12D and 12E show the electrode plate patterns for the conventional feedthrough capacitor filter 38. FIG. 12F shows the bipolar capacitor mounted on a pair of leads 28, and FIG. 12G is an electrical schematic.

More particularly, the integrated EMI filter 120 of FIGS. 12 and 13 comprises both the capacitive element 36 of the notch EMI filter 22 with the active and ground electrode plates 40 and 42 of a standard feedthrough filter capacitor 38 within a single dielectric base 44. More specifically, the feedthrough filter capacitor 38 comprises a monolithic ceramic bipolar feedthrough filter capacitor having two passageways 52 extending therethrough. These passageways are configured to receive therethrough respective conductive terminal pins or lead wires 28, and the internal diameter thereof are metalized to form a conductive link between the active electrode plates 40 of the low pass filter and the active electrode plates 54 of the capacitive element 36 of the notch EMI filter 22. As is well understood in the art, the active electrode plates 40 and 54, the ground electrode plates 42 of the feedthrough filter capacitor 38, and the ground electrode plates 56 of the capacitive element 36 of the notch EMI filter 22 are typically silk-screened onto ceramic plates forming the integrated capacitor 38. The ground electrode plates 42 of the broadband low pass EMI filter 24 extend to termination surfaces on opposite external sides of the capacitor 38, and are typically connected to one another by means of a metalized covering or base layer. Similarly, the ground electrode plates 56 of the capacitive element 36 of the notch EMI filter 22 extend outwardly to exterior surfaces of the capacitor 38 and are coupled to one another by means of external metalization 58 applied to the base 44 of the capacitor 38.

FIG. 13 is the capacitor 38 of FIG. 12 combined with a discrete inductor element 34 in accordance with the invention. It should be noted that the ground electrode plates 42 are conductively coupled to the ferrule 46, whereas the external metalization 58 allows the inductor 34 of the notch EMI filter 22 to be conductively coupled lead-to-lead between the ground electrode plates 56 of the isolated internal capacitors 50 forming the capacitive element 36 of the notch EMI filter 22.

Figure 14A:
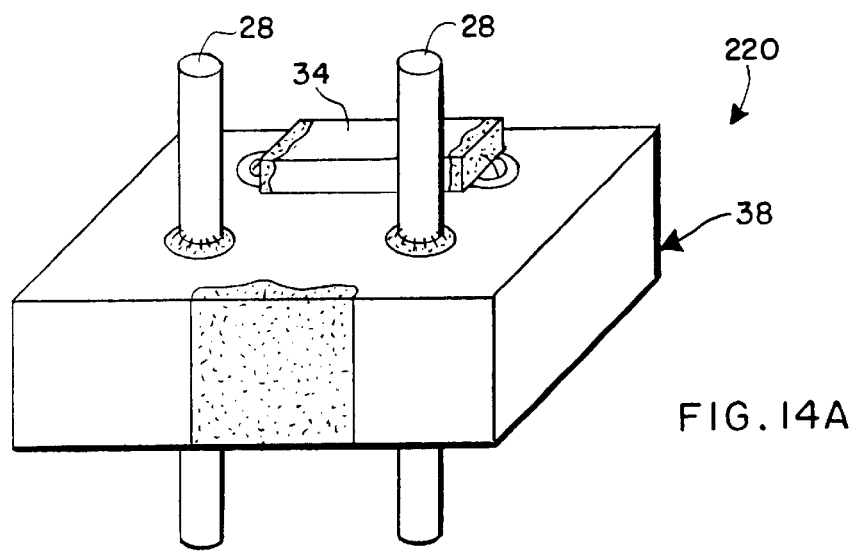
Figure 14B:
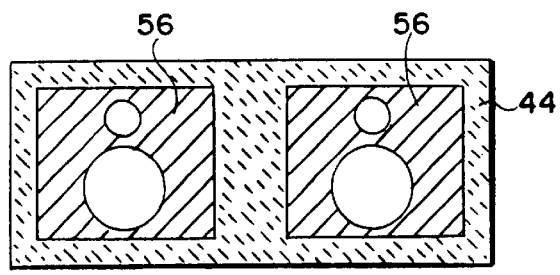
Figure 14C:
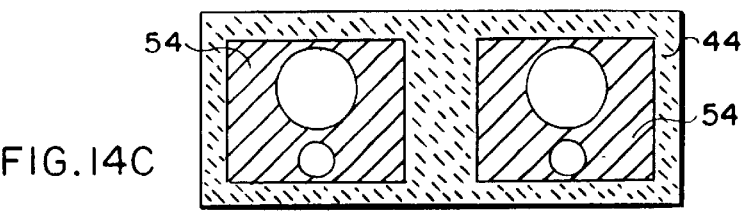
Figure 14D:
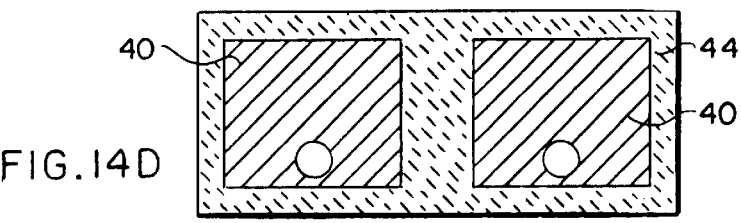
Figure 14E:
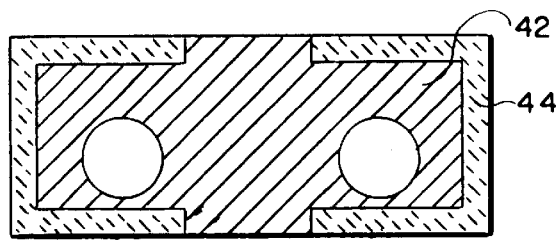

FIGS. 14A–14E show another bipolar feedthrough capacitor 38 designed similar to that illustrated in FIGS. 12A–12E, again having two integrated capacitors in accordance with the invention in a co-planar relationship. FIG. 14A is in perspective view thereof, illustrating a chip inductor 34 electrically connected to the notch filter capacitor 36. FIGS. 14B and 14C show the electrode plate patterns for the notch filter capacitor 36 in accordance with the invention. FIGS. 14D and 14E show the electrode plate patterns for the conventional feedthrough capacitor filter 38.

Figure 15A:
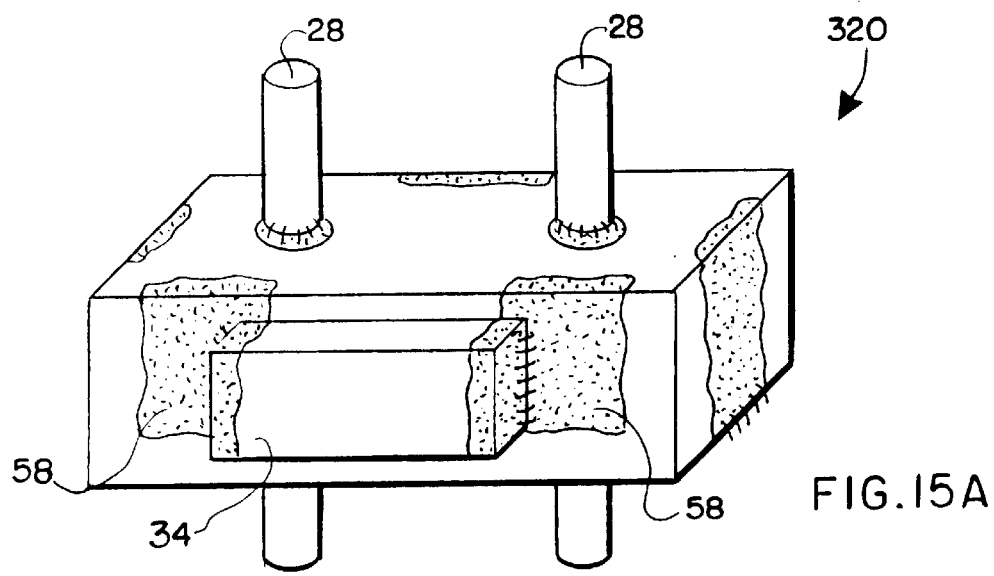
Figure 15B:
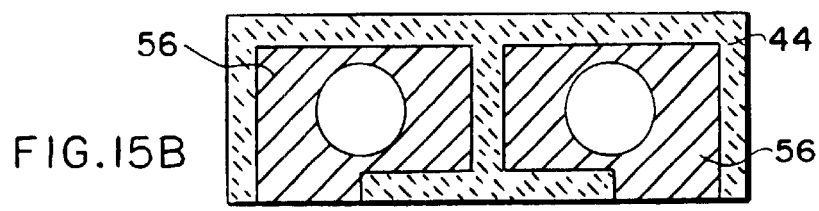
Figure 15C:
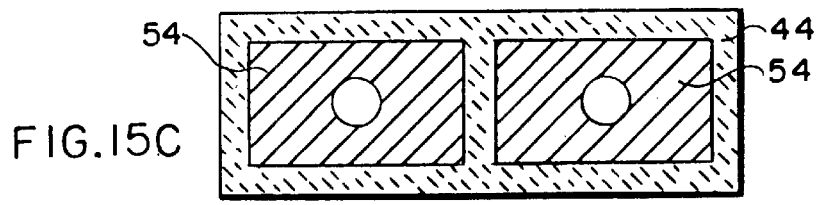
Figure 15D:
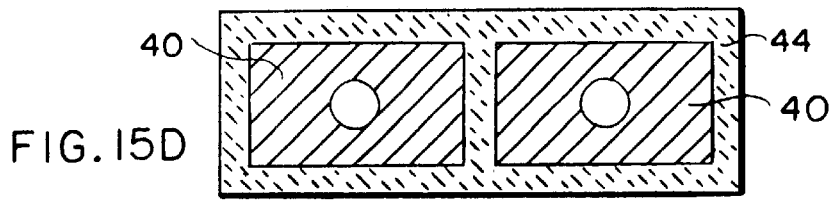
Figure 15E:
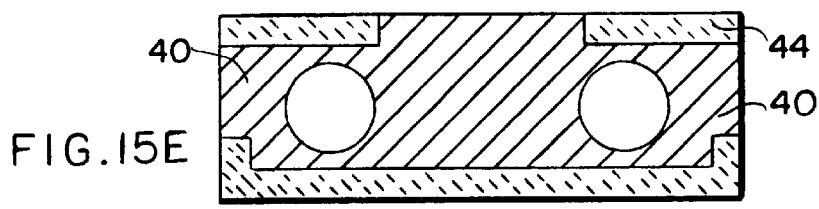
Figure 16A:
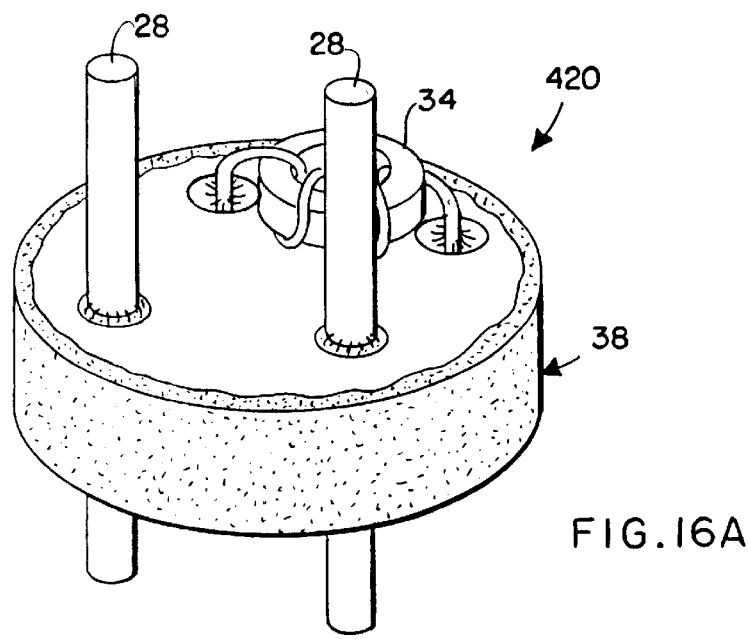

FIGS. 15A–15E illustrate yet another bipolar feedthrough capacitor similar to FIGS. 14A–14E. FIG. 15A is in perspective view thereof, illustrating a chip inductor 34 electrically connected to the notch filter capacitor. FIGS. 15B and 15C show the electrode plate patterns for the notch filter capacitor 36 in accordance with the invention. FIGS. 15D and 15E show the electrode plate patterns for the conventional feedthrough capacitor filter 38.

Figure 16B:
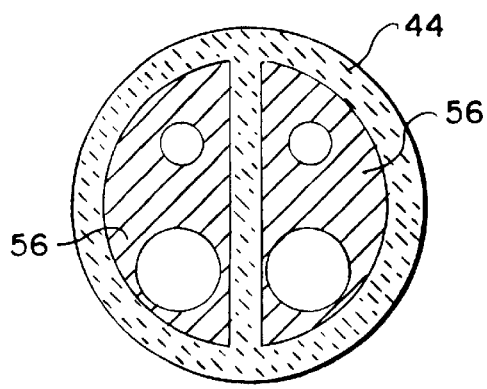
Figure 16C:
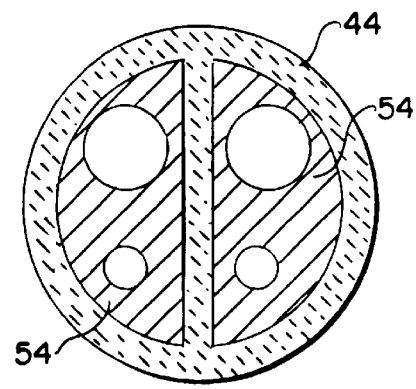
Figure 16D:
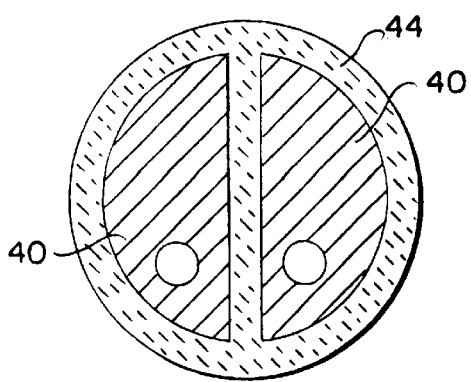
Figure 16E:
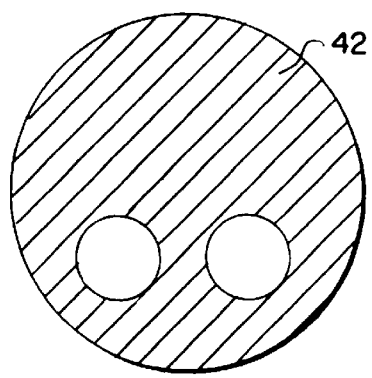

FIGS. 16A–16E show an integrated quadpolar feedthrough capacitor of an implantable defibrillator having two sensing leads 28 with notch filtering utilizing a toroidal inductor 34, and the less sensitive High Voltage outputs with no notch filter. FIGS. 16B and 16C show the electrode plate patterns for the notch filter capacitors 36 in accordance with the inventions. FIGS. 16D and 16E show the electrode plate patterns for conventional feedthrough capacitor filter 38.

Figure 17A:
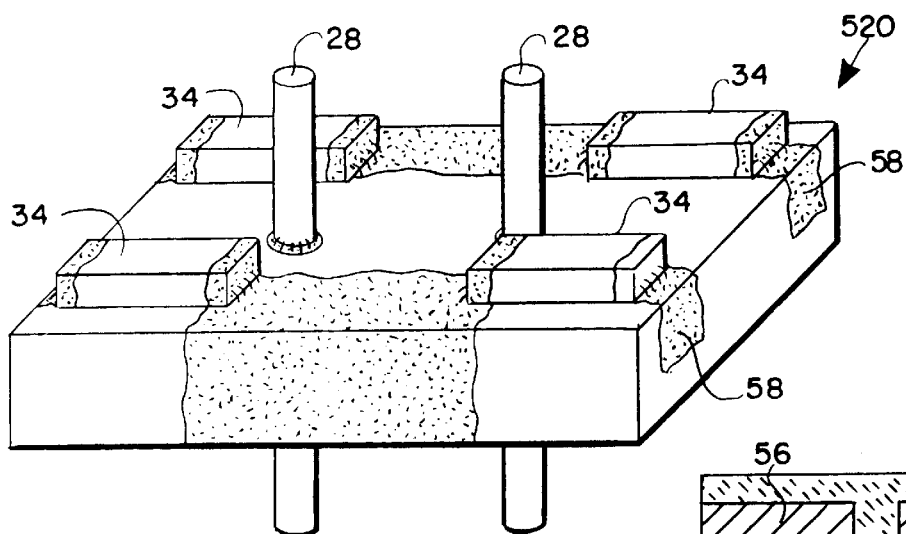
Figure 17C:
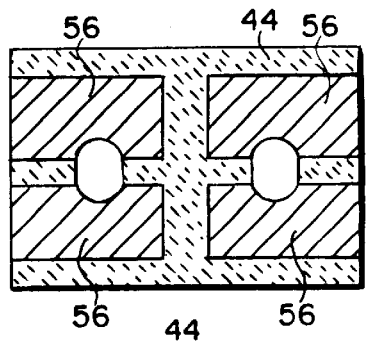
Figure 17B:
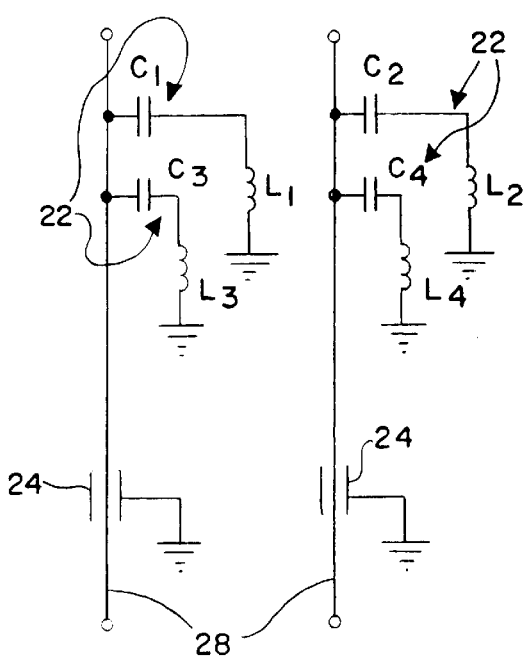
Figure 17D:
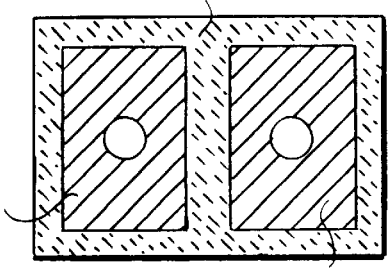
Figure 17E:
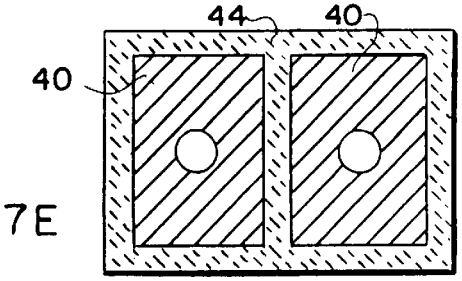
Figure 17F:
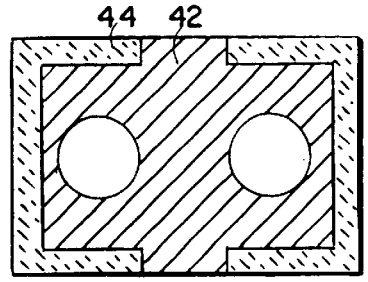

FIGS. 17A–17F illustrate a dual line to ground notch EMI filter 22 mounted on an integrated bipolar feedthrough capacitor. FIG. 17A is a perspective view thereof. FIG. 17B is an electrical schematic thereof. FIG. 17C and 17D show the electrode plate patterns for the notch filter capacitors 36 in accordance with the invention. FIGS. 17E and 17F show the electrode plate patterns for the conventional feedthrough capacitor filter 38.

FIGS. 18A–18F illustrate a quadpolar feedthrough capacitor with line to ground chip inductors 34. FIG. 18A is a perspective view thereof. FIG. 18B is an electrical schematic thereof. FIGS. 18C and 18D show the electrode plate patterns for the notch filter capacitors 36 in accordance with the invention. FIGS. 18E and 18F show the electrode plate patterns for the conventional feedthrough capacitor filters 38.

From the foregoing it will be appreciated that the present invention provides a process for providing electromagnetic capability of an electronic device while in the presence of an electromagnetic emitter operating at the same or a similar frequency or frequencies. The process provides electromagnetic compatibility of an implantable electronic medical device while in the presence of an electronic article surveillance (EAS) device operating at the same or a similar frequency or frequencies. In this case, the process steps include (1) associating a low pass broadband electromagnetic interference (EMI) filter 24 with one or more leads 28 of the implantable electronic medical device, and (2) attenuating one or more specific frequencies passing through the feedthrough filter capacitor 38 and generated by the EAS device utilizing a notch electromagnetic interference (EMI) filter 22.

In the process described above, the attenuating step may include the step of placing an L-C series resonant circuit between each lead of the electronic device and a ground. Alternatively, the attenuating step may include the step of placing paired L-C series resonant circuits between each lead of the electronic device and a ground, such that the respective value of the inductor 34 and the capacitor 36 elements are reversed in order to provide both common mode and differential mode attenuation. Further, the attenuating step may include the step of placing an L-C series resonant circuit between two leads 28 of the electronic device. Where a plurality of frequencies are of concern, the attenuating step may include the step of utilizing a plurality of notch EMI filters 22 associated with the leads 28 of the electronic device, which are capable of attenuating a plurality of specific frequencies outside the attenuation range of the broadband EMI filter 24.

As described in greater detail above, the notch EMI filter 22 may be integrated with the broadband low pass EMI filter 24. In this case, the integrated feedthrough filter capacitor 38 includes a casing 44 of dielectric material through which the leads 28 of the electronic device extend. A first set of electrode plates 40 are disposed within the casing in conductive relation with the leads 28 of the electronic device, and a second set of electrode plates 42 are disposed within the casing in non-conductive relation with the leads of the electronic device and in an alternating stack with the first set of electrode plates. A first conductive termination surface conductively couples the second set of electrode plates 42, wherein the first and second sets of electrode plates form the broadband low pass EMI filter 24. A third set of electrode plates 54 are disposed within the casing 44 in conductive relation with the leads 28 of the electronic device. A fourth set of electrode plates 56 are disposed within the casing 44 in non-conductive relation with the leads 28 of the electronic device and in an alternating stack with the third set of electrode plates 54, and a second conductive termination surface 58 is conductively coupled to the fourth set of electrode plates 56. The third and fourth sets of electrode plates 54 and 56 form the capacitive element 36 of the notch EMI filter 22.

In this case, the inductor 34 may be conductively coupled to the second conductive termination surface to form an inductive element for the notch EMI filter 22, or may be conductively coupled to the first conductive termination surface.

Accordingly, from the foregoing it should be apparent that the invention comprises the following:

An L-C series resonant notch EMI filter 22 to protect an implantable medical device from the EM field of an Electronic Article Surveillance (EAS) device 48 operating at a specific frequency. The resonant frequency of the notch EMI filter 22 is designed such that the capacitive reactance is equal and opposite to the inductive reactance at the resonant frequency. A preferred 3 dB bandwidth of the notch EMI filter element 22 is controlled by adjusting the Q of the L-C components and the resistance in the series circuit. The notch EMI filter is preferably located close to the point of lead ingress/egress at a circuit location prior to the point where the EAS signal could encounter a non-linear circuit element. It may be installed in conjunction with a hermetic terminal for medical implant applications, and in particular in conjunction with a feedthrough filter capacitor mounted onto a hermetic terminal for an implantable medical device.

The notch EMI filter may be constructed so that the capacitive element of the notch EMI filter is integrated in a co-planar relationship with the feedthrough filter capacitor. In this case, the notch EMI filter may include a capacitive element provided with metalized pads through holes or vias for convenient attachment of the inductor element, or with mounting pads or lands for convenient mounting The inductor element may be a chip inductor which is surface mounted to the pacemaker terminal board or circuit substrate, a wound wire solenoid on a ferrite core, or the inductor element may also be of toroidal wire wound construction wherein the number of inductor turns and wire size is designed such that a predetermined resistance is achieved for the purpose of controlling the 3 dB bandwidth of the notch EMI filter element.

The capacitor element may be a discrete capacitor which is mounted onto or adjacent to the hermetic terminal of the implantable medical device.

Further, the notch EMI filter may be mounted at the output of the telemetry coil of the implantable medical device in order to decouple an EAS signal before it can encounter a non-linear circuit element, or mounted at the output of the T-Coil of a hearing aid in order to decouple the EAS signal before it can encounter a non-linear circuit element. The notch EMI filter is typically mounted at the point of lead ingress/egress of the microphone or receiver of a hearing aid or cochlear implant in order to decouple the EAS signal before it can encounter a non-linear circuit element.

Either the L, C or both series elements are of hybrid circuit thick film construction. The hybrid notch EMI filter may be mounted directly onto the hermetic terminal, feedthrough capacitor or circuit substrate of an implantable medical device.

The notch EMI filters may be arranged from lead to shield/ground in pairs with the value of the L and C elements reversed in order to provide common mode and differential mode attenuation without the need for additional components.

The EAS signal referred to above may be (1) the signal emitted from an airport walkthrough security system, (2) the signal emitted from a portable metal detector, (3) the EM field emitted from a Magnetic Resonance Imager (MRI), diathermy, liptotripter, tomography or other medical treatment/imaging system, (4) any undesirable RF signal from a walkthrough or handheld security system, (5) any undesirable RF signal from emitted medical diagnostic or surgical equipment, (6) the signal emitted from an Radio Frequency Identification System (RFID), (7) any undesirable RF signal from any known or future emitter which may interfere with an implantable medical device, (8) any undesirable RF signal from any known or future emitter which may interfere with a hearing aid, cochlear implant orother hearing system, (9) any undesirable RF signal from any known or future emitter which may interfere with a neurostimulator, (10) any undesirable RF signal from any known or future emitter which may interfere with an implantable drug pump or infusion device, (11) any undesirable RF signal from any known or future emitter which may interfere with an implantable epilepsy control or general seizure control device, (12) any undesirable RF signal from any known or future emitter which may interfere with artificial limbs or muscle control devices, (13) any undesirable RF signal from any known or future emitter which may interfere with an artificial heart, artificial pancreas, artificial eye, or the like, (14) any undesirable RF signal from any known or future emitter which may interfere with an implantable ventricular assist device (VAD), (15) any undesirable RF signal from any known or future emitter which may interfere with an implantable lymphatic control pump or (16) any undesirable RF signal from any known or future emitter and the implantable medical device is any electronic device or circuit.

The implantable medical device may be a cardiac pacemaker, an implantable cardioverter defibrillator, a combined defibrillator/pacemaker, a neurostimulator, an implantable drug or infusion pump, a hearing aid, cochlear implant or other hearing system.

Finally, the notch EMI filter may be placed across the leads of a neurostimulation device in order to attenuate or decouple EAS signals from direct induction of currents to nerves or other sensitive human tissues.

The notch EMI filters described above wherein a plurality of notch EMI filters may also be employed in parallel in order to reject multiple specific frequencies.

Although several different embodiments of the invention have been described in detail for purposes of illustration, various modifications may be made without departing from the spirit and scope of the invention. Accordingly, the invention is not to be limited, except as by the appended claims.

I claim:

1. An electromagnetic interference (EMI) filter, comprising:

a broadband electromagnetic interference (EMI) filter associated with one or more leads of an electronic device and capable of attenuating a range of frequencies; and an inductor-capacitor (L-C) series resonant notch electromagnetic interference (EMI) filter associated with the leads of the electronic device and capable of attenuating a specific frequency outside the attenuation range of the broadband EMI filter;

wherein the broadband EMI filter comprises a capactive low pass filter in a feedthrough filter capacitor, comprising:

a casing of dielectric material through which the leads of the electronic device extend;

a first set of electrode plates disposed within the casing in conductive relation with the leads of the electronic device, a second set of electrode plates disposed within the casing in non-conductive relation with the leads of the electronic device and in an alternating stack with the first set of electrode plates, and a first conductive termination surface conductively coupled to the second set of electrode plates, wherein the first and second sets of electrode plates form the broadband EMI filter; and a third set of electrode plates disposed within the casing in conductive relation with the leads of the electronic device, a fourth set of electrode plates disposed within the casing in non-conductive relation with the leads of the electronic device and in an alternating stack with the third set of electrode plates, and a second conductive termination surface conductively coupled to the fourth set of electrode plates, wherein the third and fourth sets of electrode plates form the capacitive element of the notch EMI filter.

2. The EMI filter of claim 1, wherein the feedthrough filter capacitor comprises at least a portion of a hermetic terminal for an implantable medical electronic device.

3. The EMI filter of claim 1, wherein the notch EMI filter comprises an L-C series resonant circuit disposed between each lead of the electronic device and a ground.

4. The EMI filter of claim 3, wherein the notch EMI filter comprises paired L-C series resonant circuits such that the respective value of the inductor and the capacitor elements are reversed in order to provide both common mode and differential mode attenuation.

5. The EMI filter of claim 3, wherein the notch EMI filter comprises an L-C series resonant circuit extending between two leads of the electronic device.

6. The EMI filter of claim 1, wherein the notch EMI filter comprises an L-C series resonant circuit extending between two leads of the electronic device.

7. The EMI filter of claim 1, wherein the notch EMI filter comprises a plurality of notch electromagnetic interference (EMI) filters associated with the leads of the electronic device and capable of attenuating a plurality of specific frequencies outside the attenuation range of the broadband EMI filter.

8. The EMI filter of claim 1, including an inductor conductively coupled to the second conductive termination surface to form an inductive element of the notch EMI filter.

9. The EMI filter of claim 8, wherein the inductor is further conductively coupled to the first conductive termination surface.

10. The EMI filter of claim 8, wherein the inductor is conductively coupled between the second conductive termination surfaces of two leads of the electronic device.

11. The EMI filter of claim 8, wherein the inductor comprises a chip inductor.

12. The EMI filter of claim 8, wherein the second conductive termination surface is disposed in through-holes within the dielectric casing.

13. The EMI filter of claim 8, wherein the second conductive termination surface comprises a metalized pad on an exterior surface of the dielectric casing.

14. The EMI filter of claim 8, wherein the inductor comprises a wound wire solenoid on a ferrite core.

15. The EMI filter of claim 14, wherein the inductor is of toroidal wound wire construction.

16. An electromagnetic interference (EMI) filter, comprising:

a capacitive low pass broadband electromagnetic interference (EMI) filter associated with one or more leads of an electronic device and capable of attenuating a range of frequencies; and an inductor-capacitor (L-C) series resonant notch electromagnetic interference (EMI) filter associated with the leads of the electronic device and capable of attenuating a specific frequency outside the attenuation range of the broadband EMI filter, wherein a capacitive element of the notch EMI filter is integrated with the broadband EMI filter;

wherein the notch EMI filter comprises a plurality of notch electromagnetic interference (EMI) filters associated with the leads of the electronic device and capable of attenuating a plurality of specific frequencies outside the attenuation range of the broadband EMI filter.

17. An electromagnetic interference (EMI) filter, comprising:

a capacitive low pass broadband electromagnetic interference (EMI) filter associated with one or more leads of an electronic device and capable of attenuating a range of frequencies; and an inductor-capacitor (L-C) series resonant notch electromagnetic interference (EMI) filter associated with the leads of the electronic device and capable of attenuating a specific frequency outside the attenuation range of the broadband EMI filter, wherein a capacitive element of the notch EMI filter is integrated with the broadband EMI filter;

wherein the notch EMI filter comprises an L-C series resonant circuit extending between two leads of the electronic device.

18. An electromagnetic interference (EMI) filter, comprising:

a capacitive low pass broadband electromagnetic interference (EMI) filter associated with one or more leads of an electronic device and capable of attenuating a range of frequencies; and an inductor-capacitor (L-C) series resonant notch electromagnetic interference (EMI) filter associated with the leads of the electronic device and capable of attenuating a specific frequency outside the attenuation range of the broadband EMI filter, wherein a capacitive element of the notch EMI filter is integrated with the broadband EMI filter;

wherein the broadband EMI filter comprises at least a portion of a hermetic terminal for an implantable medical electronic device.

19. An electromagnetic interference (EMI) filter, comprising:

a capacitive low pass broadband electromagnetic interference (EMI) filter associated with one or more leads of an electronic device and capable of attenuating a range of frequencies; and an inductor-capacitor (L-C) series resonant notch electromagnetic interference (EMI) filter associated with the leads of the electronic device and capable of attenuating a specific frequency outside the attenuation range of the broadband EMI filter, wherein a capacitive element of the notch EMI filter is integrated with the broadband EMI filter;

wherein the notch EMI filter comprises an L-C series resonant circuit disposed between each lead of the electronic device and a ground.

20. The EMI filter of claim 19, wherein the notch EMI filter comprises paired L-C series resonant circuits such that the respective value of the inductor and the capacitor elements are reversed in order to provide both common mode and differential mode attenuation.

21. An electromagnetic interference (EMI) filter, comprising:
a capacitive low pass broadband electromagnetic interference (EMI) filter associated with one or more leads of an electronic device and capable of attenuating a range of frequencies;
an inductor-capacitor (L-C) series resonant notch electromagnetic interference (EMI) filter associated with the leads of the electronic device and capable of attenuating a specific frequency outside the attenuation range of the broadband EMI filter, wherein a capacitive element of the notch EMI filter is integrated with the broadband EMI filter;
a casing of dielectric material through which the leads of the electronic device extend;
a first set of electrode plates disposed within the casing in conductive relation with the leads of the electronic device, a second set of electrode plates disposed within the casing in non-conductive relation with the leads of the electronic device and in an alternating stack with the first set of electrode plates, and a first conductive termination surface conductively coupled to the second set of electrode plates, wherein the first and second sets of electrode plates form the broadband EMI filter; and
a third set of electrode plates disposed within the casing in conductive relation with the leads of the electronic device, a fourth set of electrode plates disposed within the casing in non-conductive relation with the leads of the electronic device and in an alternating stack with the third set of electrode plates, and a second conductive termination surface conductively coupled to the fourth set of electrode plates, wherein the third and fourth sets of electrode plates form the capacitive element of the notch EMI filter; and
an inductor conductively coupled to the second conductive termination surface to form an inductive element of the notch EMI filter.

22. The EMI filter of claim 21, wherein the inductor is further conductively coupled to the first conductive termination surface.

23. The EMI filter of claim 22, wherein the second conductive termination surface comprises a metalized pad on an exterior surface of the dielectric casing.

24. The EMI filter of claim 23, wherein the inductor comprises a chip inductor.

25. The EMI filter of claim 21, wherein the inductor is conductively coupled between the second conductive termination surfaces of two leads of the electronic device.

26. The EMI filter of claim 25, wherein the inductor comprises a chip inductor.

27. The EMI filter of claim 25, wherein the second conductive termination surface is disposed in through-holes within the dielectric casing.

28. The EMI filter of claim 27, wherein the inductor comprises a wound wire solenoid on a ferrite core.

29. A process for providing electromagnetic compatibility of an electronic device while in the presence of an electromagnetic emitter operating at the same or a similar frequency or frequencies, comprising the steps of:
associating a low pass broadband electromagnetic interference (EMI) filter with one or more leads of the electronic device;
attenuating one or more specific frequencies passing through the broadband EMI filter and generated by the electromagnetic emitter, utilizing an inductor-capacitor (L-C) series resonant notch electromagnetic interference (EMI) filter; and
integrating the notch EMI filter with the broadband EMI filter, wherein the integrated broadband and notch EMI filters comprise:
a casing of dielectric material through which the leads of the electronic device extend;
a first set of electrode plates disposed within the casing in conductive relation with the leads of the electronic device, a second set of electrode plates disposed within the casing in non-conductive relation with the leads of the electronic device and in an alternating stack with the first set of electrode plates, and a first conductive termination surface conductively coupled to the second set of electrode plates, wherein the first and second sets of electrode plates form the broadband EMI filter; and
a third set of electrode plates disposed within the casing in conductive relation with the leads of the electronic device, a fourth set of electrode plates disposed within the casing in non-conductive relation with the leads of the electronic device and in an alternating stack with the third set of electrode plates, and a second conductive termination surface conductively coupled to the fourth set of electrode plates, wherein the third and fourth sets of electrode plates form the capacitive element of the notch EMI filter.

30. The process of claim 29, wherein the attenuating step includes the step of placing paired L-C series resonant circuits between each lead of the electronic device and a ground, such that the respective value of the inductor and the capacitor elements are reversed in order to provide both common mode and differential mode attenuation.

31. The process of claim 29, wherein the attenuating step includes the step of placing an L-C series resonant circuit between two leads of the electronic device.

32. The process of claim 29, wherein the attenuating step includes the step of utilizing a plurality of notch EMI filters associated with the leads of the electronic device, which are capable of attenuating a plurality of specific frequencies outside the attenuation range of the broadband EMI filter.

33. The process of claim 29, wherein the broadband EMI filter comprises at least a portion of a hermetic terminal for an implantable medical electronic device.

34. The process of claim 29, wherein the electromagnetic emitter comprises an electronic article surveillance (EAS) device.

35. The process of claim 29, wherein the attenuating step includes the step of placing an L-C series resonant circuit between each lead of the electronic device and a ground.

36. The process of claim 29, including the step of conductively coupling an inductor to the second conductive termination surface to form an inductive element of the notch EMI filter.

37. The process of claim 36, including the step of conductively coupling the inductor to the first conductive termination surface.

38. The process of claim 36, including the step of conductively coupling the inductor between the second conductive termination surfaces of two leads of the electronic device.

39. A process for providing electromagnetic compatibility of an implantable electronic medical device while in the presence of an electronic article surveillance (EAS) device operating at the same or a similar frequency or frequencies, comprising the steps of:

associating a low pass broadband electromagnetic interference (EMI) filter with one or more leads of the implantable electronic medical device, wherein the broadband EMI filter comprises a feedthrough filter capacitor;

attenuating one or more specific frequencies passing through the feedthrough filter capacitor and generated by the EAS device utilizing a notch electromagnetic interference (EMI) filter; and integrating the notch EMI filter with the broadband EMI filter, wherein the feedthrough filter capacitor comprises:

a casing of dielectric material through which the leads of the electronic device extend;

a first set of electrode plates disposed within the casing in conductive relation with the leads of the electronic device, a second set of electrode plates disposed within the casing in non-conductive relation with the leads of the electronic device and in an alternating stack with the first set of electrode plates, and a first conductive termination surface conductively coupled to the second set of electrode plates wherein the first and second sets of electrode plates form the broadband EMI filter; and a third set of electrode plates disposed within the casing in conductive relation with the leads of the electronic device, a fourth set of electrode plates disposed within the casing in non-conductive relation with the leads of the electronic device and in an alternating stack with the third set of electrode plates, and a second conductive termination surface conductively coupled to the fourth set of electrode plates, wherein the third and fourth sets of electrode plates form the capacitive element of the notch EMI filter.

40. The process of claim 39, wherein the attenuating step includes the step of placing an L-C series resonant circuit between each lead of the electronic device and a ground.

41. The process of claim 39, wherein the attenuating step includes the step of placing paired L-C series resonant circuits between each lead of the electronic device and a ground, such that the respective value of the inductor and the capacitor elements are reversed in order to provide both common mode and differential mode attenuation.

42. The process of claim of 39, wherein the attenuating step includes the step of placing an L-C series resonant circuit between two leads of the electronic device.

43. The process of claim 39, wherein the attenuating step includes the step of utilizing a plurality of notch EMI filters associated with the leads of the electronic device, which are capable of attenuating a plurality of specific frequencies outside the attenuation range of the broadband EMI filter.

44. The process of claim 39, including the step of conductively coupling an inductor to the second conductive termination surface to form an inductive element of the notch EMI filter.

45. The process of claim 44, including the step of conductively coupling the inductor to the first conductive termination surface.

46. The process of claim 44, including the step of conductively coupling the inductor between the second conductive termination surfaces of two leads of the electronic device.

* * * * *